United States Patent
Harel et al.

(10) Patent No.: US 11,214,597 B2
(45) Date of Patent: *Jan. 4, 2022

(54) STABLE DRY POWDER COMPOSITION COMPRISING BIOLOGICALLY ACTIVE MICROORGANISMS AND/OR BIOACTIVE MATERIALS AND METHODS OF MAKING

(71) Applicant: Advanced BioNutrition Corp., Columbia, MD (US)

(72) Inventors: Mordechai Harel, Pikesville, MD (US); Roger Drewes, Hockessin, DE (US); Brian Carpenter, Baltimore, MD (US); Elena Artimovich, Columbia, MD (US)

(73) Assignee: Advanced BioNutrition Corp., Columbia, MD (US)

( * ) Notice: Subject to any disclaimer, the term of this patent is extended or adjusted under 35 U.S.C. 154(b) by 81 days.

This patent is subject to a terminal disclaimer.

(21) Appl. No.: 16/227,075

(22) Filed: Dec. 20, 2018

(65) Prior Publication Data

US 2019/0194259 A1 Jun. 27, 2019

Related U.S. Application Data

(63) Continuation of application No. 13/321,708, filed as application No. PCT/US2010/036098 on May 26, 2010, now abandoned.

(60) Provisional application No. 61/181,248, filed on May 26, 2009, provisional application No. 61/223,295, filed on Jul. 6, 2009.

(51) Int. Cl.
| | |
|---|---|
| C07K 14/00 | (2006.01) |
| A61K 9/14 | (2006.01) |
| A61K 9/19 | (2006.01) |
| A61K 47/36 | (2006.01) |
| A61K 47/38 | (2006.01) |
| A61K 47/42 | (2017.01) |
| A61K 47/46 | (2006.01) |
| C12N 1/04 | (2006.01) |
| C12N 11/04 | (2006.01) |
| A23L 33/00 | (2016.01) |
| A23L 33/135 | (2016.01) |
| A23K 40/30 | (2016.01) |
| A23K 10/18 | (2016.01) |
| A23K 50/42 | (2016.01) |
| A61K 9/06 | (2006.01) |
| C12N 1/20 | (2006.01) |
| A23L 29/00 | (2016.01) |
| A23L 33/15 | (2016.01) |
| A23K 20/174 | (2016.01) |
| A23K 20/189 | (2016.01) |
| A23K 50/80 | (2016.01) |

(52) U.S. Cl.
CPC ............ *C07K 14/001* (2013.01); *A23K 10/18* (2016.05); *A23K 20/174* (2016.05); *A23K 20/189* (2016.05); *A23K 40/30* (2016.05); *A23K 50/42* (2016.05); *A23K 50/80* (2016.05); *A23L 29/06* (2016.08); *A23L 33/135* (2016.08); *A23L 33/15* (2016.08); *A23L 33/40* (2016.08); *A61K 9/06* (2013.01); *A61K 9/143* (2013.01); *A61K 9/146* (2013.01); *A61K 9/19* (2013.01); *A61K 47/36* (2013.01); *A61K 47/38* (2013.01); *A61K 47/42* (2013.01); *A61K 47/46* (2013.01); *C12N 1/04* (2013.01); *C12N 1/20* (2013.01); *C12N 11/04* (2013.01); *Y02A 40/818* (2018.01)

(58) Field of Classification Search
None
See application file for complete search history.

(56) References Cited

U.S. PATENT DOCUMENTS

| | | | |
|---|---|---|---|
| 3,241,977 A | 3/1966 | Mitchell |
| 3,897,307 A | 7/1975 | Porubcan |
| 4,337,242 A | 6/1982 | Markus |
| 4,656,767 A | 4/1987 | Tarrant |
| 5,026,543 A | 6/1991 | Rijke |
| 5,227,373 A | 7/1993 | Alexander |
| 5,262,187 A | 11/1993 | Hahn |
| 5,407,957 A | 4/1995 | Kyle |

(Continued)

FOREIGN PATENT DOCUMENTS

| | | |
|---|---|---|
| CA | 2807997 | 2/2012 |
| CL | 9312008 | 3/2008 |

(Continued)

OTHER PUBLICATIONS

Subsequent Substantive Examination Report for Philippines Application No. 1-2014-502092, dated Jun. 14, 2019—4 pages.

(Continued)

*Primary Examiner* — Louise W Humphrey
*Assistant Examiner* — Srikanth Patury
(74) *Attorney, Agent, or Firm* — RatnerPrestia

(57) ABSTRACT

The present invention relates to embedding live or dead microorganisms and/or bioactive materials in a protective dry formulation matrix, wherein the formation includes the bioactive microorganism or material, a formulation stabilizer agent, and a protective agent. The formulation agent is prepared by dispersing all the solid components in a solution, with or without a vacuum, and cooling the solution to a temperature above its freezing temperature. The methods include a primary drying step of the formulation at a desired temperature and time period, and an accelerated secondary drying step under maximum vacuum and elevated temperature, to achieve a final desirable water activity of the dry material.

4 Claims, 11 Drawing Sheets

(56) References Cited

U.S. PATENT DOCUMENTS

| | | |
|---|---|---|
| 5,518,918 A | 5/1996 | Barclay |
| 5,637,494 A | 6/1997 | King |
| 5,658,767 A | 8/1997 | Kyle |
| 5,715,774 A | 2/1998 | Adey |
| 5,731,006 A | 3/1998 | Akiyama |
| 5,766,520 A | 6/1998 | Bronshtein |
| 5,908,622 A | 6/1999 | Barclay |
| 5,958,455 A | 9/1999 | Roser |
| 5,968,569 A | 10/1999 | Cavadini |
| 5,981,719 A | 11/1999 | Woiszwillo |
| 6,060,050 A | 5/2000 | Brown |
| 6,187,330 B1 | 2/2001 | Wang |
| 6,190,701 B1 | 2/2001 | Roser |
| 6,258,362 B1 | 7/2001 | Loudon et al. |
| 6,267,958 B1 | 7/2001 | Andya |
| 6,290,991 B1 | 9/2001 | Roser |
| 6,306,345 B1 | 10/2001 | Bronshtein et al. |
| 6,331,310 B1 | 12/2001 | Roser |
| 6,338,856 B1 | 1/2002 | Allen |
| 6,338,866 B1 | 1/2002 | Criggall |
| 6,451,567 B1 | 9/2002 | Barclay |
| 6,468,782 B1 | 10/2002 | Tunnacliffe |
| 6,503,411 B1 | 1/2003 | Franks |
| 6,509,146 B1 | 1/2003 | Bronshtein |
| 6,509,178 B1 | 1/2003 | Tanaka |
| 6,534,087 B2 | 3/2003 | Busson et al. |
| 6,537,666 B1 | 3/2003 | Bronshtein |
| 6,565,871 B2 | 5/2003 | Roser |
| 6,582,941 B1 | 6/2003 | Yokochi |
| 6,586,006 B2 | 7/2003 | Roser |
| 6,589,560 B2 | 7/2003 | Foster |
| 6,664,099 B1 | 12/2003 | Worrall |
| 6,716,460 B2 | 4/2004 | Abril |
| 6,726,934 B1 | 4/2004 | Prokop |
| 6,733,759 B2 | 5/2004 | Ivey |
| 6,790,453 B2 | 9/2004 | Porzio |
| 6,797,266 B2 | 9/2004 | Naidu |
| 6,811,792 B2 | 11/2004 | Roser |
| 6,841,181 B2 | 1/2005 | Jager |
| 6,872,357 B1 | 3/2005 | Bronshtein |
| 6,884,866 B2 | 4/2005 | Bronshtein et al. |
| 6,900,173 B2 | 5/2005 | Martin |
| 6,919,172 B2 | 7/2005 | DePablo |
| 6,964,771 B1 | 11/2005 | Rosen et al. |
| 7,005,280 B2 | 2/2006 | Barclay |
| 7,052,719 B2 | 5/2006 | Bernstein |
| 7,056,495 B2 | 6/2006 | Roser |
| 7,122,370 B2 | 10/2006 | Porubcan |
| 7,153,472 B1 | 12/2006 | Bronshtein |
| 7,258,873 B2 | 8/2007 | Truong-Le et al. |
| 7,282,194 B2 | 10/2007 | Sung |
| 7,381,425 B1 | 6/2008 | Truong-Le |
| 7,396,548 B2 | 7/2008 | Kyle |
| 7,744,925 B2 | 6/2010 | Roser |
| 7,842,310 B2 | 11/2010 | Hwang |
| 7,927,858 B2 | 4/2011 | Mayeresse |
| 7,939,105 B2 | 5/2011 | Parikh |
| 7,998,502 B2 | 8/2011 | Harel |
| 8,097,245 B2 | 1/2012 | Harel |
| 8,377,496 B2 | 2/2013 | Clinger |
| 8,460,726 B2 | 6/2013 | Harel |
| 8,834,591 B2 | 9/2014 | Rafi et al. |
| 8,834,951 B2 | 9/2014 | Harel |
| 8,871,266 B2 | 10/2014 | Crittenden et al. |
| 9,072,310 B2 | 7/2015 | Harel |
| 9,731,020 B2 | 8/2017 | Harel et al. |
| 2001/0012610 A1 | 8/2001 | Bronshtein |
| 2001/0016220 A1 | 8/2001 | Jager |
| 2002/0192202 A1 | 12/2002 | Naidu |
| 2003/0017192 A1 | 1/2003 | Kanafani et al. |
| 2003/0022333 A1 | 1/2003 | Bronshtein |
| 2003/0147898 A1 | 8/2003 | Van Nest |
| 2003/0165472 A1 | 9/2003 | McGrath et al. |
| 2003/0190332 A1 | 10/2003 | Gilad |
| 2004/0038825 A1 | 2/2004 | Leland |
| 2004/0047881 A1 | 3/2004 | Kyle |
| 2004/0062758 A1 | 4/2004 | Mayra-Makinen et al. |
| 2004/0081638 A1 | 4/2004 | Kyle |
| 2004/0081699 A1 | 4/2004 | Rademacher |
| 2004/0052895 A1 | 8/2004 | Ivey et al. |
| 2004/0175389 A1 | 9/2004 | Porubcan |
| 2004/0177392 A1 | 9/2004 | Barratt |
| 2004/0219206 A1 | 11/2004 | Roser |
| 2004/0241313 A1 | 12/2004 | Nana |
| 2005/0019417 A1 | 1/2005 | Ko |
| 2005/0032192 A1 | 2/2005 | Vesey |
| 2005/0079244 A1 | 4/2005 | Giffard |
| 2005/0100559 A1 | 5/2005 | Myatt |
| 2005/0123599 A1 | 6/2005 | Ott |
| 2005/0153018 A1 | 7/2005 | Ubbink |
| 2005/0241011 A1 | 10/2005 | Allnut |
| 2005/0266069 A1 | 12/2005 | Simmons |
| 2006/0008861 A1 | 1/2006 | Allnutt |
| 2006/0024404 A1 | 2/2006 | Kyle |
| 2006/0051408 A1 | 3/2006 | Parente Duena |
| 2006/0120999 A1 | 6/2006 | Dhar |
| 2006/0121468 A1 | 6/2006 | Allnutt |
| 2006/0127453 A1 | 6/2006 | Harel |
| 2006/0130162 A1 | 6/2006 | Kyle |
| 2006/0147500 A1 | 7/2006 | Klingeberg |
| 2006/0154067 A1 | 7/2006 | Cooper |
| 2006/0222694 A1 | 10/2006 | Oh |
| 2006/0258623 A1 | 11/2006 | Harel |
| 2006/0265766 A1 | 11/2006 | Kyle |
| 2007/0020289 A1 | 1/2007 | Mattern |
| 2007/0031534 A1 | 2/2007 | Tsujimoto |
| 2007/0048295 A1 | 3/2007 | Chen et al. |
| 2007/0082008 A1 | 4/2007 | Harel |
| 2007/0122397 A1 | 5/2007 | Sanguansri et al. |
| 2007/0196508 A1 | 8/2007 | Heuer |
| 2007/0207165 A1 | 9/2007 | Thiry |
| 2007/0211397 A1 | 9/2007 | Sokolow |
| 2007/0292952 A1 | 12/2007 | Dhar |
| 2008/0044081 A1 | 2/2008 | Lieb |
| 2008/0044481 A1 | 2/2008 | Harel |
| 2008/0050497 A1 | 2/2008 | Mai |
| 2008/0102132 A2 | 5/2008 | Giner |
| 2008/0107634 A1 | 5/2008 | Mogna |
| 2008/0112972 A1 | 5/2008 | Truong-Le |
| 2008/0131514 A1 | 6/2008 | Truong-Le |
| 2008/0193546 A1 | 8/2008 | Roser |
| 2008/0194504 A1 | 8/2008 | Kyle |
| 2008/0221231 A1 | 9/2008 | Cooper |
| 2008/0229609 A1 | 9/2008 | Broshtein |
| 2008/0241244 A1 | 10/2008 | Truong-Le |
| 2008/0261916 A1 | 10/2008 | Jaszberenyi et al. |
| 2009/0061496 A1 | 3/2009 | Kuhn et al. |
| 2009/0155351 A1 | 6/2009 | Hejl |
| 2009/0162518 A1 | 6/2009 | Clinger |
| 2009/0162521 A1 | 6/2009 | Clinger et al. |
| 2009/0181363 A1 | 7/2009 | Dhar |
| 2009/0203592 A1 | 8/2009 | Beermann et al. |
| 2009/0208585 A1 | 8/2009 | Roser et al. |
| 2009/0232894 A1 | 9/2009 | Chouvenc |
| 2009/0238890 A1 | 9/2009 | Piechocki |
| 2009/0246184 A1 | 10/2009 | Harel |
| 2009/0324636 A1 | 12/2009 | Piechocki |
| 2010/0015177 A1 | 1/2010 | Drew |
| 2010/0047393 A1 | 2/2010 | Glas et al. |
| 2010/0074994 A1 | 3/2010 | Harel |
| 2010/0086638 A1 | 4/2010 | Kyle |
| 2010/0092521 A1 | 4/2010 | Dhar |
| 2010/0120014 A1 | 5/2010 | Bronshtein |
| 2010/0120676 A1 | 5/2010 | Boehm et al. |
| 2010/0189767 A1 | 7/2010 | Shimoni |
| 2010/0242301 A1 | 9/2010 | Rampersad |
| 2010/0297231 A1 | 11/2010 | Vehring |
| 2011/0070334 A1 | 3/2011 | Rangavajla |
| 2011/0120489 A1 | 5/2011 | Pye |
| 2011/0223282 A1 | 9/2011 | BergonzelliDegonda |
| 2012/0009248 A1 | 1/2012 | Truong-Le |
| 2012/0039956 A1 | 2/2012 | Harel |
| 2012/0040010 A1 | 2/2012 | Harel |
| 2012/0114621 A1 | 5/2012 | Harel |

(56) References Cited

U.S. PATENT DOCUMENTS

| | | |
|---|---|---|
| 2012/0288483 A1 | 11/2012 | Harel |
| 2012/0322663 A1 | 12/2012 | Harel |
| 2013/0287896 A1 | 10/2013 | Harel |
| 2013/0296165 A1 | 11/2013 | Harel |

FOREIGN PATENT DOCUMENTS

| | | |
|---|---|---|
| CN | 101287449 | 10/2008 |
| CN | 101951789 | 1/2011 |
| CN | 102186360 | 9/2011 |
| EP | 0028563 | 5/1981 |
| EP | 0259739 | 3/1988 |
| EP | 0471904 | 2/1992 |
| EP | 1110462 | 6/2001 |
| EP | 1344458 | 9/2003 |
| GB | 1232057 | 5/1971 |
| GB | 2389787 | 12/2003 |
| JP | 57114527 | 7/1982 |
| JP | 05246856 | 9/1993 |
| JP | 06022746 | 2/1994 |
| JP | 08511956 | 12/1996 |
| JP | 11506467 | 6/1999 |
| JP | 11513700 | 11/1999 |
| JP | 2001505431 | 4/2001 |
| JP | 2002512970 | 5/2002 |
| JP | 2002530321 | 9/2002 |
| JP | 2004506437 | 3/2004 |
| JP | 2004525106 | 8/2004 |
| JP | 2004528288 | 9/2004 |
| JP | 2005501268 | 1/2005 |
| JP | 2005519600 | 7/2005 |
| JP | 2005270100 | 10/2005 |
| JP | 2005534741 | 11/2005 |
| JP | 2007519796 | 7/2007 |
| JP | 2007522085 | 8/2007 |
| JP | 2009522280 | 6/2009 |
| JP | 2010512755 | 4/2010 |
| JP | 2010-227125 A | 10/2010 |
| KR | 20050105669 | 11/2005 |
| KR | 1020050106559 | 11/2005 |
| RU | 2277905 | 6/2006 |
| RU | 2374859 | 12/2009 |
| RU | 2 410 084 C1 | 1/2011 |
| WO | 9640077 | 12/1996 |
| WO | 9824327 | 6/1998 |
| WO | 9824882 | 6/1998 |
| WO | 0112779 | 2/2001 |
| WO | 0136590 | 5/2001 |
| WO | 2001036590 | 5/2001 |
| WO | 0215720 | 2/2002 |
| WO | 02058735 | 8/2002 |
| WO | 02061111 | 8/2002 |
| WO | 02076391 | 10/2002 |
| WO | 03086454 | 10/2003 |
| WO | 03087327 A2 | 10/2003 |
| WO | 03088755 | 10/2003 |
| WO | 03089579 | 10/2003 |
| WO | 03103692 | 12/2003 |
| WO | 2004022728 | 3/2004 |
| WO | 2004024177 | 3/2004 |
| WO | 2004039417 | 5/2004 |
| WO | 2004043139 | 5/2004 |
| WO | 2004080196 | 9/2004 |
| WO | 2004091307 | 10/2004 |
| WO | 2004112767 | 12/2004 |
| WO | 2004112776 | 12/2004 |
| WO | 2005030229 | 4/2005 |
| WO | 2005084646 | 9/2005 |
| WO | WO 2005/060937 | 9/2005 |
| WO | 2005105978 | 11/2005 |
| WO | 2005115341 | 12/2005 |
| WO | 2005117962 | 12/2005 |
| WO | 2006085082 | 8/2006 |
| WO | 2006122299 | 11/2006 |
| WO | WO 2007/035455 | 3/2007 |
| WO | 2007038926 | 4/2007 |
| WO | 2007067207 | 6/2007 |
| WO | 2007/079147 A2 | 7/2007 |
| WO | 2007/084059 A1 | 7/2007 |
| WO | 2007075988 | 7/2007 |
| WO | 2007084500 | 7/2007 |
| WO | 2007117511 | 10/2007 |
| WO | 2007/136553 A2 | 11/2007 |
| WO | 2008016214 | 2/2008 |
| WO | 2008/056983 A1 | 5/2008 |
| WO | 2008076975 | 6/2008 |
| WO | 2009002481 | 12/2008 |
| WO | 2009020455 | 2/2009 |
| WO | 2009140327 | 11/2009 |
| WO | 2010002418 | 1/2010 |
| WO | 2010046321 | 4/2010 |
| WO | 2010111347 | 9/2010 |
| WO | 2010118188 | 10/2010 |
| WO | 2010118205 | 10/2010 |
| WO | 2010125084 | 11/2010 |
| WO | 2010135495 | 11/2010 |
| WO | 2010138522 | 12/2010 |
| WO | 2011094469 | 8/2011 |
| WO | 2012021783 A2 | 2/2012 |

OTHER PUBLICATIONS

Final Office Action for U.S. Appl. No. 15/687,730, dated Jun. 24, 2019—21 pages.
Korean Office Action for Korean Application No. 10-2024-7029648, dated Jun. 11, 2019, with translation—20 pages.
Substantive Examination Report Stage I for Indonesian Application No. P00201705802, dated Jun. 13, 2019, with translation—4 pages.
Vietnamese Office Action for Application No. 1-2012-01991, dated Sep. 3, 2019 with translation, 3 pages.
Office Action for Canadian Application No. 2,866,889, dated Apr. 1, 2019.
Chinese Office Action for Chinese Application No. 201710034705.9, dated Dec. 3, 2019, with translation, 16 pages.
Mazur et al., Macromolecules, 47:771-6 (2014).
Niness, J. Nutr., 129:1402S-6S (1999).
Shin et al., J. Food Science, 65(5):884-7 (2000).
Sucrose, Sucrose Structure, Webpage, Elmhurst College (2003).
Canadian Office Action for Canadian Application No. 2,763,074, dated Oct. 22, 2018, 4 pages.
Communication of Notice of Opposition of EP Application No. 10781100.2, dated May 23, 2018, 1 page.
Notice of Opposition to European Patent Application No. 10781100.2, dated Apr. 26, 2018, 34 pages.
Harel and Tang, "A Novel Preservation and Delivery Technology for Live Probiotics, Enzymes and Vitamins", XVIIth International Conference on Bioencapsulation, 2 pages (Sep. 24-26, 2009).
Nazarro, Journal of Functional Foods I, pp. 319-323 (2009).
Kurtmann, Cryobiology, 58:175-80 (2009).
Lone Kurtmann, "Viability of Dried Lactic Acid Bacteria: Relation Between Physical State of Freeze-Drying", Thesis by Lone Kurtmann, 69 pages (2009).
Carlsen, Cryobiology, 6 pages (2009).
Kurtmann et al., Biotechnol. Prog., 25(1):265-70 (2009).
Kurtmann et al., "The Browning of Freeze-Dried Probiotic Bacteria Cultures and Its Relation to the Loss of Viability During Storage", University of Copenhagen, 30 pages (2009).
Morgan et al., Journal of Microbiological Methods, 66:183-93 (2006).
Higl et al., Biotechnol. Prog., 23:794-800 (2007).
First Examination Report for Indian Patent Application No. 7257/DELNP/2012, dated Jan. 11, 2018 (with English Translation).
Office Action for Russian Patent Application No. 2014136089, dated Feb. 14, 2018 (with English Translation).
Substantive Examination Report II for Indonesia Patent Application No. W00201300512, dated Mar. 8, 2018.
Substantive Examination Report for Philippines Application No. 1-2014-502092, dated Feb. 6, 2018.

(56) References Cited

OTHER PUBLICATIONS

Indonesian Substantive Examination Report for Indonesian Application No. W00201202694, dated Nov. 27, 2017 with translation, 3 pages.
European Communication Pursuant to Araticle 94(3) for European Application No. 13764138.7, dated Dec. 18, 2017, 5 pages.
Chinese Office Action for Chinese Application No. 201380015928. 0, dated Nov. 3, 2017 with transtation, 10 pages.
Chilean Office Action for Chilean Application No. 201402506, dated Oct. 16, 2017 with translation, 13 pages.
Russian Office Action for Russian Application No. 2014136089/15, dated Sep. 22, 2017 with translation, 7 pages.
Indian Office Action for Indian Application No. 824/DELNP/2013, dated Oct. 18, 2017 with translation, 7 pages.
Indian Examination Report for Indian Appliction No. 9996/DELNP/2011, dated Sep. 12, 2017 with translation, 8 pages.
European Examination Report for European Application No. 07865743. 4, dated Oct. 6, 2017, 3 pages.
Non Final Office Action for U.S. Appl. No. 15/269,171, dated Oct. 16, 2017, 61 pages.
Vietnamese Office Action for Vi etnam Application No. 1-2011-03487, dated May 15, 2017, with translation, 3 pages.
Russian Office Action for Russian Application No. 2014136089/15(058394), dated May 17, 2017 with translation, 13 pages.
European Communication for European Application No. 07865743. 4, dated Mar. 2, 2017, 4 pages.
Australian Examination Report for Australian Application No. 2013234931, dated Mar. 21, 2017, 3 pages.
Chinese Office Action for Chinese Application No. 201380015928. 0, dated Apr. 5, 2017 with translation, 10 pages.
Chilean Office Action for Application No. 2506-14, dated Jan. 24, 2017, 9 pages.
Notice of Allowance for U.S. Appl. No. 14/644,248, dated Mar. 15, 2017, 11 pages.
Mexican Office Action for Mexican Application No. MX/a/2013/001535, dated Nov. 29, 2016, 3 pages.
Australian Examination Report for Australian Application No. 2013234931, dated Dec. 7, 2016, 4 pages.
A Korean Office Action for Korean Application No. 10-2011-7031038, dated Dec. 27, 2016 with translation, 15 pages.
Canadian Office Action for Canadian Application No. 2,785,815, dated Oct. 14, 2016, 3 pages.
Chinese Office Action for Application No. 201380015928.0, dated Nov. 14, 2016 with translation, 8 pages.
Notice of Allowance for U.S. Appl. No. 13/260,661, dated Dec. 2, 2016, 24 pages.
Chilean Office Action for Chilean Application No. 00759-2009, dated Dec. 12, 2016 with translation, 4 pages.
Canadian Offic e Action dated Sep. 9, 2016 for Canadian Application No. 2756883, 4 pages.
Tian, J et al., "Chitosan microperes as candidate plasmid vaccine carrier for oral immunisation of Japanese flounder (*Paralichthys olivaceus*)" Dec. 15, 2008, pp. 220-229, vol. 126, Nos. 3-4, Veterinary Immunology and Immunopathology.
Kumar, S.R et al., "Potential use of chitosan nanoparticles for oral delivery of DNA vaccine in Asian sea bass (*Lates calcarifer*) to protect from Vibrio (*Listonella*) anguillarum", Jul. 2008, pp. 47-56, vol. 25, Nos. 1-2, Fish & Shell Immunology.
European Examination Report, for EP Application No. 11817090.1, dated Jul. 15, 2016, 6 pages.
Indonesian Examination Report for Indonesian Application No. W00 2013 00512, dated Jun. 30, 2016, 4 pages.
Indonesian Examination Report for Indonesian Application No. W00 201104583, dated Jun. 27, 2016, 4 pages.
Mexican Office Action for Mexican Application No. MX/a/2013/001535, dated Jul. 13, 2016 with translation, 4 pages.
Korean Office Action for Korean Application No. 10-2011-7031038, dated Jun. 27, 2016, 9 pages.
Canadian Examination Report for Canadian Application No. 2763074, dated Jun. 14, 2017, 4 pages.

Non-Final Office Action for U.S. Appl. No. 14/644,248, dated Jul. 15, 2016, 58 Pages.
European Office Action for European Application No. 10756891.1, dated Jun. 22, 2016, 5 Pages.
Notification of Reexamination of Chinese Application No. 201080029392.4, dated Jul. 13, 2016, 10 Pages.
Final Office Action for U.S. Appl. No. 13/260,661, dated Jun. 1, 2016.
Canadian Office Action dated Mar. 10, 2016 for Canadian Application No. 2,763,074.
Chinese Office Action dated Feb. 26, 2016 for Chinese Application No. 201380015928.0 with translation.
Chinese Search Report dated Feb. 23, 2016 for Chinese Application No. 2013800115928.0 with translation.
Chinese Office Action dated Apr. 1, 2016 for Chinese Application No. 201410326898.1 with translation.
Final Office Action dated Feb. 3, 2016 for U.S. Appl. No. 13/849,941.
Non Final Office Action dated Feb. 3, 2016 for U.S. Appl. No. 14/456,130.
Philippine Office Action dated Jan. 14, 2016 for Philippine Application No. 1-2011-502445.
Non Final Office Action dated Jan. 12, 2016 for U.S. Appl. No. 14/479,791.
Canadian Office Action dated Dec. 8, 2015 for Canadian Application No. 2,756,883.
Chinese Reexamination Report dated Dec. 23, 2015 for Chinese Application No. 201080029392.4 with translation.
Aral, C. et al., "Alternative approach to the preparation of chitosan beads," International Journal of Pharmaceutics 168 (1998) 9-15.
Bodmeier, R., et al., "Preparation and evaluation of drug-containing chitosan beads," Drug Development and Industrial Pharmacy, 15(9), 1989, 1475-1494.
Bradford, M., "A rapid and sensitive method for the quantitation of microgram quantities of protein utilizing the principle of protein-dye binding," Analytical biochemistry 72 (1976) 248-254.
Calvo, P., et al., "Novel hydrophilic chitosan-polyethylene oxide nanoparticles as protein carriers," Journal of Applied Polymer Science, 63 (1997) 125-132.
Canadian Office Action dated Sep. 8, 2015 for Canadian Application No. 2,785,815.
Chopra, S. et al., 2006. Advances and potential applications of chitosan derivatives as mucoadhesive biomaterials in modern drug delivery, J. Pharm. Pharmacol. 58(8), 1021-1032.
Dang, J.M., Leong, K.W., 2006. Natural polymers for gene delivery and tissue engineering. Adv. Drug Deliv. Rev. 58(4), 487-499.
Davis, S.S., 2006. The use of soluble polymers and polymer microparticles to provide improved vaccine responses after parenteral and mucosal delivery. Vaccine 24(2), 7-10.
Entire patent prosecution history of U.S. Appl. No. 13/260,661, filed, Nov. 2, 2011, entitled, "Microparticulated Vaccines for the Oral or Nasal Vaccination and Boostering of Animals Including Fish."
European Office Action dated Nov. 6, 2015 for European Application No. 11817090.1.
Examination Report on Patent Application for Chilean Application No. 759-09 dated Mar. 27, 2009.
Huang, Y.C., et al., "Optimizing formulation factors in preparing chitosan microparticles by spray-drying method," Journal of Microencapsulation, vol. 20, No. 2 (2003) 247-260.
International Search Report for Application No. PCT/US2010/028767 dated Dec. 23, 2010.
Kang, M.L. et al., Pluronic F127 enhances the effect as an adjuvant of chitosan microspheres in the intranasal delivery of Bordetella bronchiseptica antigens containing dermonecrotoxin. Vaccine 25(23), 4602-4610.
Kim, T.J., et al., 2007. Stimulation of mucosal and systemic antibody responses against recombinant transferrin-binding protein B of Actinobacillus pleuropneumoniae with chitosan after tracheal administration in piglets. J. Vet. Med. Sci. 69(5), 535-539.
Li, X., et al., "Preparation of alginate coated chitosan microparticles for vaccine delivery," BMC Biotechnology 8:89 (2008).
Malik, D.K., et al., 2007. Recent advances in protein and peptide drug delivery systems. . Curr. Drug Deliv. 4(2), 141-151.

(56) References Cited

OTHER PUBLICATIONS

Non-Final Office Action dated Oct. 27, 2015 in U.S. Appl. No. 13/208,459.
Panos, I., et al., "New drug delivery systems based on chitosan," Current Drug Discovery Technologies, 5 (2008) 333-341.
Rege, P., et al., "Spray-dried chitinosans Part I: preparation and characterization," International Journal of Pharmaceutics 252 (2003) 41-51.
Shiraishi, S., et al.,. "Controlled release of indomethacin by chitosan-polyelectrolyte complex: optimization and in vivo/in vitro evaluation," Journal of Controlled Release 25 (1993) 217-225.
Shu, X., et al., "A novel approach to prepare tripolyphosphate/chitosan complex beads for controlled release drug delivery," International Journal of Pharmaceutics 201 (2000) 51-58.
Tobar et al., Oral vaccination of Atlantic Salmo salar against Salmon Rickettsial Septicaemia, World Aquaculture Society's 2008 annual international conference (May 19-23, 2008).
van der Lubben, I.M., et al., 2001. Chitosan microparticles for oral vaccination: preparation, characterization and preliminary in vivo uptake studies in murine Peyer's patches. Biomaterials 22(7), 687-694.
van der Lubben, I.M., et al., 2001. Chitosan for mucosal vaccination. Advanced Drug Delivery Reviews 52 (2), 139-144.
Zhou, S., et al., "Poly-D, L-lactide-co-poly(ethylene glycol) microspheres as potential vaccine delivery systems," Journal of Controlled Release 86 (2003) 195-205.
Substantive Examination Adverse Report dated Sep. 15, 2015 in Malaysian Application No. PI 2013000306.
Japanese Office Action dated Oct. 7, 2015 in Japanese Application No. 2012-551295, including English translation.
Singapore Search Report and Written Opinion dated Sep. 9, 2015 for Application No. 11201405478V.
Japanese Office Action dated Sep. 15, 2015 for Japanese Application No. 2012-513183, including English translation.
New Zealand Office Action dated Jun. 24, 2015 in New Zealand Application No. 628912.
Russian Office Action dated Jul. 21, 2015 in Russian Application No. 2013110833/13(016008).
Mexican Office Action dated Jul. 20, 2015 in Mexican Application No. MX/a/2012/008795.
Office Action dated Jun. 30, 2015 in Vietnamese Application No. 1-2011-03487.
Substantive Examination Adverse Report dated Jun. 30, 2015 in Malaysian Application No. PI 2011005733.
Office Action dated May 22, 2015 in U.S. Appl. No. 13/849,941.
Philippine Substantive Examination Report dated Mar. 20, 2015 in Philippine Application No. 1/2011/502445.
Extended European Search Report for European Application No. 13764138.7-1460 dated Apr. 9, 2015.
Japanese Office Action dated Mar. 31, 2015 in Japanese Application No. 2012-513183.
Chinese Office Action dated Mar. 2, 2015 in Chinese Application No. 201180007562.3.
Japanese Office Action dated Mar. 2, 2015 in Japanese Application No. 2012-551295.
Notice of Allowance dated Feb. 9, 2015 in U.S. Appl. No. 13/351,343.
Australian Patent Examination Report dated Jan. 23, 2015 in Patent Application No. 2010254235.
Notice of Allowance dated Jan. 15, 2015 in U.S. Appl. No. 13/911,636.
Russian Office Action dated Dec. 18, 2014 in Application No. 2011151788/10(077759).
Benedict, R.G. et al., "Preservation of Microorganisms by Freeze-Drying I. Cell Supernatant, Naylor-Smith Solution, and Salts of Various Acids as Stabilizers for Serratia marcascens," Appl. Microbiol. 1958, vol. 6, No. 6, pp. 401-407.
European Office Action for Application No. 10 781 100.2-1403 dated Oct. 17, 2014.
Extended European Search Report for European Application No. 11817090.1-1358 dated Jun. 16, 2014.
International Search Report for International Application No. PCT/US2010/036098 dated Feb. 14, 2011.
International Search Report for International Application No. PCT/US2011/022821 dated Oct. 25, 2011.
Maltrin M100 Maltodrexin, 2006, XP055120984, Internet retrieves from the Internet: URL: http://www.tpipremixes.com/productpdfs/Maltodextrin.pdf, retrieved on Jun. 2, 2014.
Perry, Stephen F, "Freeze-Drying and Cryopreservation of Bacteria," Molecular Biotechnology, 1998, vol. 9, No. 1, pp. 59-64.
Notice of Allowance dated Oct. 27, 2014 in U.S. Appl. No. 13/459,408.
Office Action dated Oct. 27, 2014 in U.S. Appl. No. 13/208,459.
International Preliminary Report on Patentability and Written Opinion for PCT International Application No. PCT/US2013/033505 dated Sep. 23, 2014.
Canadian Office Action dated Oct. 10, 2014 in Canadian Application No. 2,785,815.
Abdelwahed et al., Advanced Drug Delivery Reviews, 58:1688-1713 (2006).
Anal et al. "Recent advances in microencapsulation of probiotics for industrial applications and targeted delivery." Trends in Food Science and Technology, vol. 18, No. 5, Apr. 29, 2007, pp. 240-251.
Anderson, J.W., Johnstone, B.M. and Remley, D.T. (1999). Breast-feeding and cognitive development: a meta-analysis. Am J Clin Nutr, 70, 525-35.
Bazan, N.G. and Rodriguez de Turco E.B. (1994). Review: pharmacological manipulation of docosahexaenoic-phospholipid biosynthesis in photoreceptor cells: implications in retinal degeneration. J. Ocul Pharmacol, 10, 591-604.
Bazan, N.G. and Scott, B.L. (1990). Dietary omega-3 fatty acids and accumulation of docosahexaenoic acid in rod photoreceptor cells of the retina and at synapses. Ups J Med Sci Suppl, 48, 97-107.
Behrens, P. and Kyle, D. (1996). Microalgae as a source of fatty acids. J Food Sci, 3, 259-272.
Bergogne et al., Molecular Crystals and Liquid Crystals, 354: 79-89 (2000).
Boswell KDB, Gladue R, Prima B, Kyle DJ (1992) SCO production of fermentive microalgae. In: Kyle DJ, Ratledge C (eds) Industrial Applications of Single Cell Oils. American Oil Chemists Society, Champaign, IL., pp. 274-286.
Canadian Office Action dated Apr. 6, 2011 in Canadian Application No. 2,673,120.
Chen, et al., "Beneficial Effect of Intracellular Trehalsose on the Membrane Integrity of Dried Mammalian Cells", Cryobiology vol. 43, pp. 168-181, 2001.
Chen et al., China Tropical Medicine, 7(4):654-55 (2007) (with partial English translation).
Chinese Search Report dated May 26, 2014 for application No. 201180039219.7 filed Aug. 12, 2011.
Crawford, M.A., Costeloe, K., Ghebremeskel, K. and Phylactos, A. (1998). The inadequacy of the essential fatty acid content of present preterm feeds [published erratum appears in Eur J. Pediatr Feb. 1998; 157(2):160]. Eur J Pediatr, 157 Suppl 1, S23-7.
Crowe, J.H., Carpenter, J.F., and Crowe, L.M. (1998). "The role of vitrification in anhydrobiosis." Annu. Rev Physiol. 60:73-103.
Crowe, J.H., Crowe., L.M.., and Mouriadian, R., 1983, Cryobiology, 20, 346-356.
Crowe et al., "Anhydrobiosis: A Strategy for Survival", Adv. Space Res vol. 12, No. 4, pp. 239-247, 1992.
De Giulio, et al., "Use of alginate and cryo-protective sugars to improve the viability of lactic acid and bacteria after freezing and freeze-drying",World Journal of Microbiology and Biotechnology, Kluwer Academic Publishers, DO, vol. 21, No. 5, July 1. 2005, pp. 739-746.
Desai et al., Pharmaceutical Research, 13(12):1838-45 (1996).
Entire patent prosecution history of U.S. Appl. No. 12/519,860, filed Dec. 2, 2009, entitled, "Dry Food Product Containing Live Probiotic," now U.S. Pat. No. 8,460,726.
Entire prosecution history of U.S. Appl. No. 12/159,407, filed Nov. 21, 2008, entitled, "Delivery Vehicle for Probiotic Bacteria Comprising a Dry Matrix of Polysaccharides, Saccharides and Polyols in a Glass Form and Methods of Making Same," now U.S. Pat. No. 8,097,245.

(56) References Cited

OTHER PUBLICATIONS

Entire prosecution history of U.S. Appl. No. 13/208,459, filed Aug. 12, 2011, entitled, "Dry Storage Stabilizing Composition for Biological Materials."
Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same."
Entire prosecution history of U.S. Appl. No. 13/378,106, filed Mar. 29, 2012, entitled, "Dry Glassy Composition Comprising a Bioactive Material," now U.S. Pat. No. 8,834,951.
Entire prosecution history of U.S. Appl. No. 13/459,408, filed Apr. 30, 2012, entitled,"Delivery Vehicle for Probiotic Bacteria Comprising a Dry Matrix of Polysaccharides, Saccharides and Polyols in a Glass Form and Methods of Making Same."
Entire prosecution history of U.S. Appl. No. 13/849,941, filed Mar. 25, 2013, entitled Stablizing Composition for Biological Materials.
Entire prosecution history of U.S. Appl. No. 13/911,636, filed Jun. 6, 2013, entitled, "Dry Food Product Containing Live Probiotic."
Entire prosecution history of U.S. Appl. No. 14/456,130, filed Aug. 11, 2014, entitled, "Dry Glassy Composition Comprising a Bioactive Material."
Entire prosecution history of U.S. Appl. No. 14/479,791, filed Sep. 8, 2014, entitled, "Dry Food Product Containing Live Probiotic."
Esquisabel et al., 1997, J. Microencapsulation, 14, 627-638.
Favaro-Trindade et al., "Microencapsulation of L. acidophilus (La-05) and B. lactis (Bb-12) and evaluation of their survival at the pH values of the stomach and in bile", J. Microencapsulation, vol. 19, pp. 485-494, 2002.
First Office Action with a Search Report issued by the State Intellectual Property Office of the Peoples Republic of China dated May 22, 2013 for Chinese Application No. 201180007562.3 (with English Translation).
Grinstead G, Tokach M, Dritz, S, Goodband R, Nelssen J (2000) Effects of Spirulina platensis on growth performance of weanling pigs. Animal Feed Sci Technol 83:237-247.
He ML, Hollwich W, Rambeck WA (2002) Supplementation of algae to the diet of pigs: a new possibility to improve the iodine content in the meat. J Animal Physiol Animal Nutri 86:97-104.
Hughes, V.X. and Hillier, S.L. (1990). "Microbiologic characteristics of Lactobacillus products used for colonization of the vagina." Obstet Gynecol. 75:244-248.
Ikemoto, A., Kobayashi, T., Watanabe, S. and Okuyama, H. (1997). Membrane fatty acid modifications of PC12 cells by arachidonate or docosahexaenoate affect neurite outgrowth but not norepinephrine release. Neurochem Res, 22, 671-8.
International Preliminary Report on Patentability for PCT International Application No. PCT/US2011/022821 dated Jul. 31, 2012.
International Search Report for International Application No. PCT/US2006/49434 dated Sep. 26, 2007.
International Search Report for International Application No. PCT/US2007/087771 dated May 16, 2008.
Japanese Office Action for Japanese Patent Application No. 2008-548729, dated Jul. 23, 2012 (with English translation).
Japanese Office Action issued in Japanese Application No. 2013-524242, dated Jan. 21, 2014 (English tranlsation only).
Kailasapathy et al., "Survival and therapeutic potential of probiotic organisms with reference to Lactobacillus acidophilus and *Bifidobacterium* spp.," Immunology Cell Biology, 78, pp. 80-88, 2000.
Kearney, et al., "Enhancing the Viability of Lactobacillus plantarum Inoculum by Immobilizing the Cells in Calcium-Alginate Beads Incorporation Cryoprotectants", Applied and Environmental Microbiology, vol. 56, No. 10, Oct. 1990, pp. 3112-3116.
Kets et al., "Citrate increases glass transition temperature of vitrified sucrose preparations," Cryobiology 48 (2004), 46-54.
Krallish et al., "Effect of xylitol and trehalose on dry resistance of yeasts", Appl. Microbiol Biotechnol. 47, pp. 447-451, 1997.

Krasaekoopt et al. "Evaluation of encapsulation techniques of probiotics for yoghurt." International Dairy Journal 13, 2003. pp. 3-13.
Liao et al., "Protective Mechanism of Stabilizing Excipients against Dehydration in the Freeze-Drying of Proteins", Pharmaceutical Research, vol. 19, No. 12, pp. 1854-1861, 2002.
Linders et al., "Effect of Added Carbohydrates on Membrane Phase Behavior and Survival of Dried Lactobacillus plantarum", Cryobiology 35, pp. 31-40, 1997.
M. Le Meste, et al., 2002, Glass Transition and Food Technology: A Critical Appraisal, Journal of Food Science, 67:2444-2458.
Marteau et al., "Protection from gastrointestinal diseases with the use of probiotics", Am J Clin Nutr. 73, pp. 430S-436S, 2001.
Martinez, M. (1990). Severe deficiency of docosahexaenoic acid in peroxisomal disorders: a defect of delta 4 desaturation. Neurology, 40, 1292-8.
Office Action for Patent Application JP 2009-541634 dated Jun. 25, 2012 (with English translation).
Perdigon et al., "Lactic Acid Bacteria and their Effect on the Immune System", Curr Issues Intest Microbiol. 2, pp. 27-42, 2001.
Qiu et al., "Permeability of the infective juveniles of Steinernema carpocapsae to glycerol during osmotic dehydration and its effect on biochemical adaptation and energy metabolism", Comparative Biochemistry & Physiology, Part B, vol. 125, pp. 411-419, 2000.
Sanchez et al., 1999, Intl. J. Pharm. 185, 255-266.
Second Office Action issued by the State Intellectual Property Office of the Peoples Republic of China dated Feb. 8, 2014 in Chinese Application No. 2011800756,3, including a Search Report (with English translation).
Selmer-Olsen, et al., "Survival of Lactobacillus helveticus entrapped in Ca-alginate in relation to water content, storage and rehydration", Journal of Industrial Microbiology & Biotechnology, vol. 23, 1999, pp. 79-85.
Shah, N.P. (2000). "Probiotic bacteria: selective enumeration and survival in dairy foods." Journal of Dairy Science. 83:894-907.
Stordy, BJ. (1995). Benefit of docosahexaenoic acid supplements to dark adaptation in dyslexics. Lancet, 346 (8971): 385.
Supplementary European Search Report for European Appln. No. 11737688 dated Sep. 18, 2013.
Sutas et al., "Probiotics: effects on immunity", Am J Clin Nutr. 73, pp. 444S-450S, 2001.
Tobar et al., Oral Vaccination of Atlantic Salmon Salmo salar against Salmon Rickettsial Septicaemia, presentation, World Aquaculture Society/s 2008 annual international conference (May 19-23, 2008).
Tobar et al., Oral Vaccination of Atlantic Salmon Salmo salar against Salmonid rickettsial septicaemia (SRS), abstract, World Aquaculture Society/s 2008 annual international conference (May 19-23, 2008).
Wong, Recent Patents on Drug Delivery & Formation 3:8-25 (2009).
Xu, L.Z., Sanchez, R., Sali, A. and Heintz, N. (1996). Ligand specificity of brain lipid-binding protein. J Biol Chem, 271, 24711-9.
Zarate et al. ("Viability and biological properties of probiotic vaginal lactobacilli after lyophilization and refrigerated storage into gelatin capsules," Process Biochemistry 41 (2006), 1779-1785.
Substantive Examination Adverse Report dated Aug. 29, 2014 in counterpart Malaysian Application No. PI 2011005733.
Office Action dated Aug. 6, 2014 in corresponding Russian Application No. 2011151788/10(077759).
Japanese Office Action dated Aug. 1, 2014 in corresponding Japanese Application No. 2012-513183, with translation.
Office Action dated Mar. 21, 2014 in corresponding Russian patent application, with translation.
Supplementary European Search report corresponding with Application No. EP 10 78 1100 dated Sep. 28, 2012.
New Zealand Examination Report dated May 18, 2012.
Annear, D., "The preservation of leptospires by drying from the liquid state," Journal of General Microbiology, 27 (1962) 341-343.

(56) References Cited

OTHER PUBLICATIONS

Capela, P., et al., "Effect of cryoprotectants, prebiotics and microencapsulation on survival of probiotic organisms in yoghurt and freeze-dried yoghurt," Food Research International, 39 (2006) 203-211.
Hincha, D., et al., "Protection of liposomes against fusion during drying by oligosaccharides is not predicted by the calorimetric glass transition temperatures of the dry sugars," European Biophysics Journal, 37 (2008) 503-508.
Morgan, C., et al., "Preservation of micro-organisms by drying; a review," Journal of Microbiological Methods, 66 (2006) 183-193.
Schwab, C., et al., "Influence of oligosaccharides on the viability and membrane properties of lactobacillus reuteri TMW1.106 during freeze-drying," Cryobiology, 55 (2007) 108-114.
Chinese Office Action for Chinese Applicaton No. 201380015928.0, dated Mar. 3, 2021, with translation, 20 pages.
Ünlü, C., et al., "Use of lactobacilli and estriol combination in a treatment of disturbed vaginal ecosystem: a review," 2011, 12: 239-46, J Turkish-German Gynecol Assoc.
Argentina Substantive Examination Report for Argentina Application No. PI 30100304, dated Jun. 2, 2021, 10 pages.
Argentina Substantive Examination Report for Argentina Application No. P110100304, dated Jun. 2, 2021, 4 pages.
Melczer et al., "Experience with Local Ecotherapy in the Treatment of Bacterial Vaginosis In Pregnant and Non-Pregnant Women", Journal of Hungarian Association of Obstetrics and Gynecology [Magyar Nöorv Labj], 2003, vol. 65, pp. 319-323.

STABLE DRY POWDER COMPOSITION COMPRISING BIOLOGICALLY ACTIVE MICROORGANISMS AND/OR BIOACTIVE MATERIALS AND METHODS OF MAKING

CROSS-REFERENCE TO RELATED APPLICATION

This application is a continuation of U.S. application Ser. No. 13/321,708, filed Feb. 6, 2012, which is a U.S. National Phase Application of PCT International Application PCT/US2010/036098, filed May 26, 2010, which claims priority to U.S. Provisional Application Nos. 61/181,248 and 61/223,295 filed in the United States Patent and Trademark Office on May 26, 2009 and Jul. 6, 2009, respectively, the contents of which are hereby incorporated by reference herein for all purposes.

BACKGROUND OF THE INVENTION

Field of the Invention

The present invention is in the field of protection of bioactive microorganism and/or materials in high temperature and humid conditions. In particular, the invention relates to embedding live microorganisms and/or bioactive materials in a protective dry formulation matrix.

Related Background Art

Bioactive microorganisms, such as live or dead bacteria and viruses, or bioactive materials, such as proteins, vitamins, minerals, hormones and cells are generally unstable when stored under conditions of high temperature and humidity. For example, many commercially available probiotic bacteria such as *Lactobacillus rhamnosus* can loose more than one log of viability in less than two weeks when stored in ambient atmosphere at room temperature (approximately 25° C.). A common process to dry and protect these bioactive microorganisms after harvesting from a culture vessel (e.g., fermentor) is to drop a concentrated solution of the living cells into liquid nitrogen then store the frozen beads in −80° C. refrigeration for later freeze drying or shipment to other locations. Freeze-drying has been a dominant method for drying sensitive bioactive material. Other methods, such as spray drying, supercritical fluid drying, and desiccation are generally not suitable for sensitive bioactives such as live or attenuated bacteria and viruses because of the high drying temperatures used in these methods which result in significant damage to the microorganism itself. In addition, they may not sufficiently dry the material to the specific residual moisture requirements for product stability, and thus an additional drying step by other means, may be required.

In freeze-drying, the bioactive microorganism or materials is commonly mixed in a solution or suspension of protective agents, frozen, and then dehydrated by sublimation under full vacuum. The low temperatures of the freeze-drying process decrease the degradation reactions of the bioactive and minimize the loss of activity in the final dry form. However, the requirement for sub-zero temperatures is energy intensive, and the low surface area to volume ratios of the frozen material necessitates the use of long drying time (up to several days per batch cycle). The slow drying of the freeze-drying process also facilitates the formation of ice crystals that can damage or denature a sensitive bioactive. For this reason, bioactive microorganism or materials such as viruses, bacteria, and cells that possess a cell wall or lipid membrane, pose significant challenges to the freeze-drying process.

One option to reduce the formation of an ice crystal structure is to add cryoprotective agents to the bioactive solution. Such protective agents are highly soluble chemicals that are added to a formulation to protect cell membranes and intracellular proteins during freezing and to enhance stability during storage. Common stabilizers for live bacteria and viruses include sugars such as sucrose, glycerol, or sorbitol, at high concentrations with the cellular material or bioactive (Morgan et al., 2006; Capela et al., 2006). However, such protective agents may not penetrate adequately into the cell to protect active components within the intracellular volume. Therefore, a significant challenge remains to develop an optimal drying process and formulation that minimizes drying losses while achieving adequate storage stability of the dried material.

Some of the problems associated with the freeze-drying have been resolved by using a combination of certain formulations and vacuum drying in a liquid state. Annear (Annear 1962) developed a formulation containing bacteria in a solution of sugars and amino acids and a vacuum drying process that involves boiling and foam formation. Roser et al. (U.S. Pat. No. 6,964,771) disclosed a similar concept of drying by foam formation that includes a liquid concentration step followed by boiling and foaming the concentrated solution (syrup) under vacuum. To mitigate the oxidation and denaturation damage that can occur during the boiling step, Bronshtein (U.S. Pat. Nos. 5,766,520, 7,153,472) introduced an improved protective formula containing carbohydrates and surfactants. The drying of the protective solution also involved a stepwise process of concentration under a moderate vacuum before application of a strong vacuum to cause frothy boiling of the remaining water to form dry stable foam. In an attempt to eliminate the boiling step, Busson and Schroeder (U.S. Pat. No. 6,534,087) have proposed a drying process in a liquid state formulation for insensitive bioactives using a vacuum oven without boiling, by applying very mild vacuum pressure above 30 Torr. After achieving a certain level of drying without boiling the material, heat was applied at above 20° C. and dried material was harvested after only a few hours.

This type of drying process, in which the bioactive solution is maintained in a liquid state during the entire drying process, has the advantage of faster drying due to convection of the liquid during boiling and the increased surface area presented by the foaming surfaces. However, boiling and foaming require input of a significant amount of heat to provide the necessary eruption of the solution. Such a drying process is not well adapted to drying of sensitive biologicals, such as viable viruses, cells or bacteria because the applied heat accelerates enzymatic processes (e.g., proteolysis), and chemical processes (e.g., oxidation and free radical attacks), which can destroy the activity or viability of the biological material.

The drying process described above is also limited in its ability to be scaled to a large industrial process. The avoidance of freezing requires the process to be conducted at lower vacuum level (>7 Torr) than in conventional freeze drying or spray freeze drying process cycles. The most significant disadvantage of the above processes is the inability to control and limit the expansion of the foam within the vessel, tray or vial. The uncontrollable eruption and often-excessive foam formation makes it practically impossible to develop an industrial scale process. The eruption and foaming nature of the boiling step results in a portion of material being splattered on the walls of the vessel and into the drying chamber. To soften the eruption during boiling, Bronshtein (U.S. Pat. Nos. 6,884,866, 6,306,345) has proposed special chambers and a controlled temperature/pressure application protocol that reduces overheating to an acceptable level. Another approach to contain the eruption and excessive foaming is described in US. Pat. App. No.: 2008/0229609, in which the bioactive solution is enclosed in a container or a bag covered with breathable membranes. Once again, these protocols are difficult to implement in industrial level and they are difficult to reliably replicate with different formulations.

A need remains for a suitable protective formulation that can be dried in a liquid state and an industrially scaleable method to dry bioactive microorganisms such as live or dead viruses, bacteria and cells, particularly at temperatures above freezing. There is a need particularly for a cost effective scaleable drying process that is also suitable for applications outside the pharmaceutical industry such as food and agriculture industries. Protective formulations and mild drying processes are required to provide adequate drying without exposure to high temperatures. A composition is needed that can protect such biologicals in storage under high temperature and humid conditions. The present invention, as described below, provides a solution to all of these challenges.

SUMMARY OF THE INVENTION

The present invention includes compositions and methods for preserving bioactive materials, such as peptides, proteins, hormones, vitamins, minerals, drugs, microbiocides, fungicides, herbicides, insecticides, spermicides, nucleic acids, antibodies, vaccines, and/or bioactive microorganism such as bacteria (probiotic or otherwise), viruses and/or cell suspensions, in storage. The drying methods provide a process of controllable expansion of a formulation comprising the bioactive microorganism or material, a formulation stabilizer agent, and a protective agent. The formulation is prepared by dispersing all the solid components in a solution, with or without a vacuum. The solution is cooled to a temperature above its freezing temperature and dried under vacuum into a dry composition, which exhibits an unexpectedly high stability. The methods include a primary drying step of the formulation at a desired temperature and time period, and an accelerated secondary drying step under maximum vacuum and elevated temperature, to achieve a final desirable water activity of the dry material.

In one embodiment, the formulation comprises sufficient amounts of formulation stabilizer agents, in which the microorganisms are embedded. Examples of a suitable formulation stabilizer agent include, but are not limited to, cellulose acetate phthalate (CAP), carboxy-methyl-cellulose, pectin, sodium alginate, salts of alginic acid, hydroxyl propyl methyl cellulose (HPMC), methyl cellulose, carrageenan, guar gum, gum acacia, xanthan gum, locust bean gum, chitosan and chitosan derivatives, collagen, polyglycolic acid, starches and modified starches, cyclodextrins and oligosaccharides (inulin, maltodextrins, dextrans, etc.); and combinations thereof.

In one particular embodiment, the preferred formulation stabilizer agent is sodium alginate. Preferably, the formulation comprises, in percent by weight of total dry matter, 0.1-10%, preferably 1-6%, more preferably 2-4% of formulation stabilizer agent. In an additional embodiment, the formulation stabilizer comprises a mixture of sodium alginate and oligosaccharides in a weight ratio of 1:1-10, more preferably 1:1-5 of sodium alginate/oligosaccharides. In yet another embodiment of the present invention, the formulation stabilizer is cross-linked with divalent metals ions to form a firm hydrogel.

In another embodiment, the formulation comprises significant amounts of protecting agents, in which the microorganisms are embedded. Examples of a suitable protecting agent include but not limited to proteins such as human and bovine serum albumin, egg albumen, gelatin, immunoglobulin, isolated soya protein, wheat protein, skim milk powder, caseinate, whey protein and any protein hydrolysates; carbohydrates including monosaccharides (e.g., galactose, D-mannose, sorbose, etc.), disaccharides (e.g., lactose, trehalose, sucrose, etc.), an amino acid such as lysine, monosodium glutamate, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols, (e.g. glycerin, erythritol, glycerol, arabitol, xylitol, sorbitol, and mannitol); propylene glycol; polyethylene glycol; pluronics; surfactants; and combinations thereof.

In one preferred embodiment, the protecting agent comprises a mixture of a disaccharide, a protein, and a protein hydrolysate. In a particular embodiment, the preferred protecting agent is a mixture of trehalose, soy protein isolate or whey protein and their hydrolysates. Preferably, the formulation comprises, in percent by weight of total dry matter, 10-90%, of trehalose, 0.1-30% soy protein isolate or whey proteins and 0.1-30% soy or whey protein hydrolysate. Preferably 20-80% of trehalose, 0.1-20% soy protein isolate or whey proteins and 1-20% soy or whey protein hydrolysate, more preferably 40-80% of trehalose, 0.1-20% soy protein isolate or whey proteins and 1-20% soy or whey protein hydrolysate.

The method of the invention typically includes blending with or without a vacuum, concentrated solution or dry powder of bioactive microorganism (e.g., live or dead vaccines, bacteria, algae, viruses and/or cell suspensions) or a bioactive material (e.g., peptides, proteins, hormones, vitamins, minerals, drugs, microbiocides, fungicides, herbicides, insecticides, spermicides, nucleic acids, antibodies, vaccines), a stabilizer agent, and a protective agent into a homogeneous formulation, cooling the formulation to a temperature above its freezing temperature, and drying under vacuum at a shelf temperature above 20° C. According to the invention, the drying process can involve a primary vacuum drying at a shelf temperature of 20° C. or above, followed by an accelerating secondary drying of the formulation under maximum vacuum and elevated temperature for a time sufficient to reduce the water activity of the dried formulation to 0.3 Aw or less.

In one embodiment of the mixing method the bioactive microorganism or material is in a dry stabilized form and is further dry blended with the dry stabilizer agents and protective agents. This dry blend is then added to water and mixed under the appropriate vacuum and agitation to give a homogeneous slurry of the desired density.

In another embodiment of the mixing method, the bioactive microorganism or material is in the form of a concentrated solution or paste. The solution is mixed with all the other formulation ingredients before adding to water.

In yet another embodiment of the mixing method, the bioactive microorganism or material is in the form of dry powder. The dry powder is mixed with all the other formulation ingredients before adding to water.

In another embodiment of the mixing method, the dry bioactive microorganism or material is mixed with just a portion of the formulation ingredients, and this mixture is added to the pre-formed slurry, prepared from the addition of the other formulation ingredients to water.

In preferred embodiments of the drying methods, the bioactive microorganism is mixed under vacuum in a solution including a formulation stabilizer agent and a protective agent. In one particular embodiment, the bioactive microorganism comprises live bacteria (e.g., probiotic bacteria). Examples of suitable microorganisms include, but are not limited to, yeasts such as *Saccharomyces, Debaromyces, Candida, Pichia* and *Torulopsis*, moulds such as *Aspergillus, Rhizopus, Mucor, Penicillium* and *Torulopsis* and bacteria such as the genera *Bifidobacterium, Clostridium, Fusobacterium, Melissococcus, Propionibacterium, Streptococcus, Enterococcus, Lactococcus, Kocuriaw, Staphylococcus, Peptostrepococcus, Bacillus, Pediococcus, Micrococcus, Leuconostoc, Weissella, Aerococcus, Oenococcus* and *Lactobacillus*. Specific examples of suitable probiotic microorganisms would be represented by the following species and include all culture biotypes within those species: *Aspergillus niger, A. oryzae, Bacillus coagulans, B. lentus, B. licheniformis, B. mesentericus, B. pumilus, B. subtilis, B. natto, Bacteroides amylophilus, Bac. capillosus, Bac. ruminocola, Bac. suis, Bifidobacterium adolescentis, B. animalis, B. breve, B. bifidum, B. infantis, B. lactis, B. longum, B. pseudolongum, B. thermophilum, Candida pintolepesii, Clostridium butyricum, Enterococcus cremoris, E. diacetylactis, E faecium, E. intermedius, E. lactis, E. muntdi, E. thermophilus, Escherichia coli, Kluyveromyces fragilis, Lactobacillus acidophilus, L. alimentarius, L. amylovorus, L. crispatus, L. brevis, L. case 4 L. curvatus, L. cellobiosus, L. delbrueckii ss. bulgaricus, L farciminis, L. fermentum, L. gasseri, L. helveticus, L. lactis, L. plantarum, L. johnsonii, L. reuteri, L. rhamnosus, L. sakei, L. salivarius, Leuconostoc mesenteroides, P. cereviseae (damnosus), Pediococcus acidilactici, P. pentosaceus, Propionibacterium fivudenreichii, Prop. shermanii, Saccharomyces cereviseae, Staphylococcus carnosus, Staph. xylosus, Streptococcus infantarius, Strep. salivarius ss. thermophilus, Strep. thermophilus* and *Strep. lactis*.

In preferred methods, the formulation is mixed under vacuum at room temperature (e.g., from 20° C. to 30° C.). After mixing to homogeneity, the formulation is then cooled to a temperature above the freezing temperature of the formulation. Typically, the formulation is cooled to between −10° C. to +10° C., more preferably the formulation is cooled to between −5° C. and +5° C. In a preferred embodiment, the cooled formulation is then transferred to a drying chamber where heating is applied (20° C. or more) while controlling an initial vacuum pressure at a level to maintain the original pre-cooling temperature. Typically, the desirable vacuum pressure is below 7 Torr but no less than 3 Torr. Under these preferred conditions a controlled expansion of the formulation and subsequent faster primary drying of the formulation is achieved. To accelerate the secondary drying, a maximum vacuum pressure is applied and heat supply temperature may be further elevated to from 30° C. to 60° C. To maximize the stability of the final product the formulation is preferably dried for a time sufficient to reduce the water activity of the formulation to Aw=0.3 or less. In a preferred embodiment of the invention, the secondary drying comprises removal of water at a pressure of less than 1 Torr, and in an especially preferred embodiment to less than 0.2 Torr.

The wet formulation can be in the form of viscous slurry or hydrogel particles ranging from 0.05 to 10 mm. The dried formulation can be used directly as a flake, or ground into a powder with an average particle size from about 10 μm to about 1000 μm. The formulation can be administrated directly to an animal, including human, as a concentrated powder, as a reconstituted liquid, (e.g., beverage), or it can be incorporated either in flake or powder form into an existing food or feed product.

DETAILED DESCRIPTION OF THE INVENTION

Definitions

Figure 1:
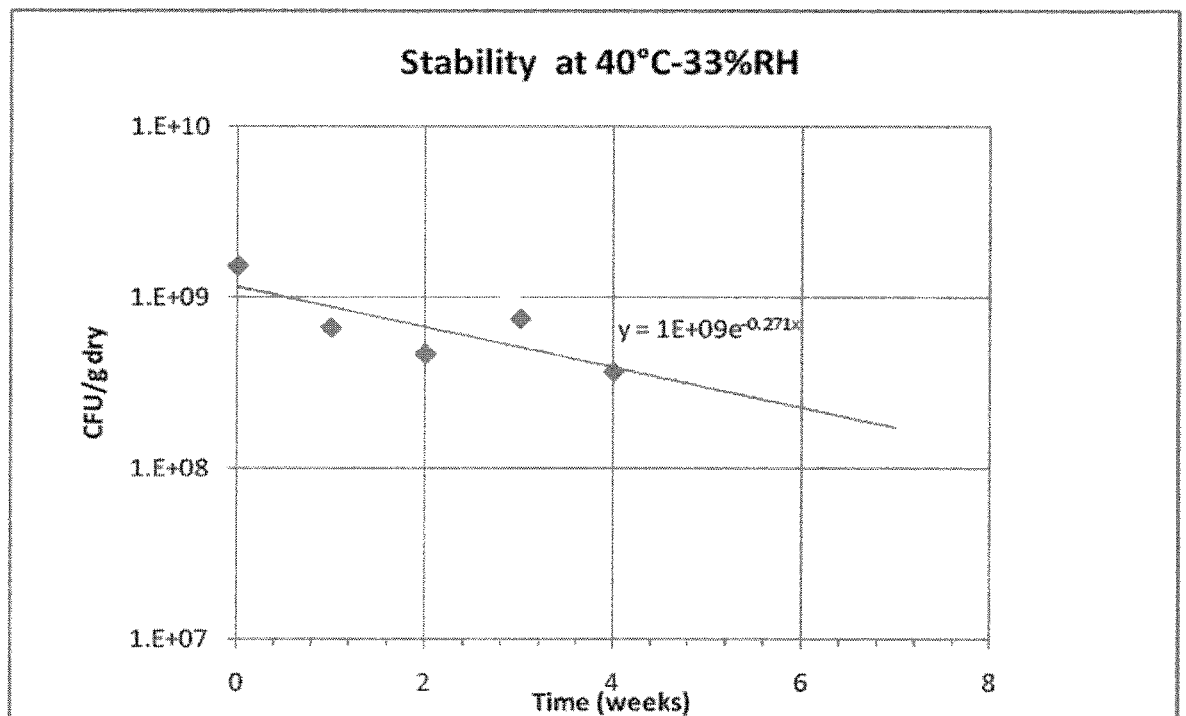
FIG. 1 shows the stability trend of the probiotic bacteria, *L. rhamnosus*, which was subjected to storage at 40° C. and 33% relative humidity.

It is to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a protein" includes singular protein or a combination of two or more proteins; reference to "enzyme", "vitamin", "bacteria", etc., includes singular or mixtures of several, and the like.

In describing and claiming the present invention, the following terminology will be used in accordance with the definitions set out below.

"Ambient" room temperatures or conditions are those at any given time in a given environment. Typically, ambient room temperature is 22-25° C., ambient atmospheric pressure, and ambient humidity are readily measured and will vary depending on the time of year, weather and climactic conditions, altitude, etc.

"Degassing" refers to the release of a gas from solution in a liquid when the partial pressure of the gas is greater than the applied pressure. This is not boiling, and can often occur at pressures above a pressure that would boil a solution. For example, bottled carbonated soft drinks contained a high partial pressure of $CO_2$. Removing the bottle cap reduces the partial pressure and the drink bubbles vigorously (it degasses, but does not boil).

"Boiling" refers to the rapid phase transition from liquid to gas that takes place when the temperature of a liquid is above its boiling temperature. The boiling temperature is the temperature at which the vapor pressure of a liquid is equal to the applied pressure. Boiling can be particularly vigorous when heat is added to a liquid that is already at its boiling point.

"Water activity" or "Aw" in the context of dried formulation compositions, refers to the availability of water and represents the energy status of the water in a system. It is defined as the vapor pressure of water above a sample divided by that of pure water at the same temperature. Pure distilled water has a water activity of exactly one or $A_w = 1.0$.

"Relative Humidity" or "RH" in the context of storage stability refers to the amount of water vapor in the air at a given temperature. Relative humidity is usually less than that required to saturate the air and expressed in percent of saturation humidity.

"Primary drying", with regard to processes described herein, refers to the drying that takes place from the time of initial vacuum application to the point where secondary drying starts. Typically, the bulk of primary drying takes place by extensive evaporation, while the product temperature remained significantly lower than the temperatures of the heat source.

"Secondary drying", with regard to processes described herein, refers to a drying step that takes place at temperatures above freezing temperatures of the formulation and near the temperature of the heat source. In a typical formulation drying process, a secondary drying step reduces the water activity of the formulation to an Aw of 0.3 or less.

"Bioactive microorganism," or "biologically active microorganism or formulation" refers to live or dead microorganism preparations, which are in such a form as to permit the biological activity of the microorganism to be unequivocally effective. "Live microorganism as dry powder" refers to a bacterial biomass in which at least 10% W/W is live bacteria. "Dead microorganism as dry powder" refers to a bacterial biomass in which at least 99.999% is dead bacteria.

"Bioactive material", "bioactive composition", "biologically active material" or "bioactive formulation" refers to preparations, which are in such a form as to permit the biological activity of the bioactive ingredients to be unequivocally effective. Such bioactive materials include but not limited to peptides, proteins, hormones, vitamins, minerals, drugs, microbiocides, fungicides, herbicides, insecticides, spermicides, nucleic acids, antibodies, and vaccines.

"Stabilizer or Stabilizing agent" refers to compounds or materials that are added to the formulation to increase the viscosity of the wet formulation or to form a hydrogel. Examples of a suitable stabilizer agent include but are not limited to polysaccharides, such as, cellulose acetate phthalate (CAP), carboxy-methyl-cellulose, pectin, sodium alginate, salts of alginic acid, hydroxyl propyl methyl cellulose (HPMC), methyl cellulose, carrageenan, guar gum, gum acacia, xanthan gum, locust bean gum, chitosan and chitosan derivatives, collagen, polyglycolic acid, starches and modified starches, cyclodextrins and oligosaccharides (inulin, maltodextrins, raffinose, dextrans, etc.) and combinations thereof.

"Protecting agent" or "protective agent" or "protectant" generally refers to compounds or materials that are added to ensure or increase the stability of the bioactive material during the drying process and afterwards, or for long-term storage stability of the dry powder product. Suitable protectants are generally readily soluble in a solution and do not thicken or polymerize upon contact with water. Suitable protectants are described below and include, but are not limited to, proteins such as human and bovine serum albumin, whey protein, soy protein, caseinate, gelatin, immunoglobulins, carbohydrates including monosaccharides (galactose, D-mannose, sorbose, etc.), disaccharides (lactose, trehalose, sucrose, etc.), an amino acid such as monosodium glutamate, lysine, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols (e.g., glycerin, erythritol, glycerol, arabitol, xylitol, sorbitol, and mannitol); propylene glycol; polyethylene glycol; Pluronics; surfactants, and combinations thereof.

A "stable" formulation or composition is one in which the bioactive microorganism or material therein essentially retains its viability, and/or biological activity upon storage. Stability can be measured at a selected temperature and humidity conditions for a selected time period. Trend analysis can be used to estimate an expected shelf life before a material has actually been in storage for that time period. For live bacteria, for example, stability is defined as the time it takes to loose 1 log of CFU/g dry formulation under predefined conditions of temperature, humidity and time period.

"Viability" with regard to bacteria, refers to the ability to form a colony (CFU or Colony Forming Unit) on a nutrient media appropriate for the growth of the bacteria. Viability, with regard to viruses, refers to the ability to infect and reproduce in a suitable host cell, resulting in the formation of a plaque on a lawn of host cells.

The compositions and methods of the present invention solves the problem of providing a cost effective and industrially scalable drying processes for producing a dry formulation containing bioactive microorganisms or materials, such as live or dead vaccines, bacteria, algae viruses and/or cell suspensions, peptides, proteins, hormones, vitamins, minerals, drugs, microbiocides, fungicides, herbicides, insecticides, spermicides, nucleic acids, antibodies, vaccines with a significantly extended lifetime in the dry state. The invention provides a formulation comprising a bioactive microorganism or material with a stabilizer agent and a protecting agent in a solution, cooling said formulation to a temperature above its freezing temperature, and stabilizing the formulation by removing the moisture under a regimen of reduced pressure while supplying heat to the composition.

Most of the viability loss of microorganism during drying processes can be attributed to a combination of freeze-thaw stresses and ice crystal formation, high osmotic and oxidative stresses, shear forces and energy release during bubble cavitations associated with the "boiling" of the solution under low drying pressure and high temperature. The present invention provides a formulation and an industrially scalable drying process that minimizes losses during the drying and protects the bioactive microorganism under harsh storage conditions thereafter.

Compositions of the Invention

The present invention includes formulation compositions of a bioactive microorganism or material, a stabilizer agent and a protecting agent in a viscous solution. The formulations of the invention were found to be inherently different in their physical structure and function from non-viscous or concentrated formulations that were dried without pre-cooling. For example, formulations of the prior art were initially "foamed" to facilitate effective drying. The foaming step generally resulted in an extensive boiling and eruption of the solution that is an unavoidable consequence of the vacuum drying in a liquid state and as a result, only a very low loading capacity of material in a vial or a vessel can be achieved (see for example U.S. Pat. No. 6,534,087, in which the thickness of the final foamed product is less than 2 mm). The compositions and drying methods of the present invention allow only a limited and controlled expansion of the formulation thereby enabling much higher loading of material per drying area and, as a result, can be easily scaled up to the production of large quantities of material.

Figure 2:
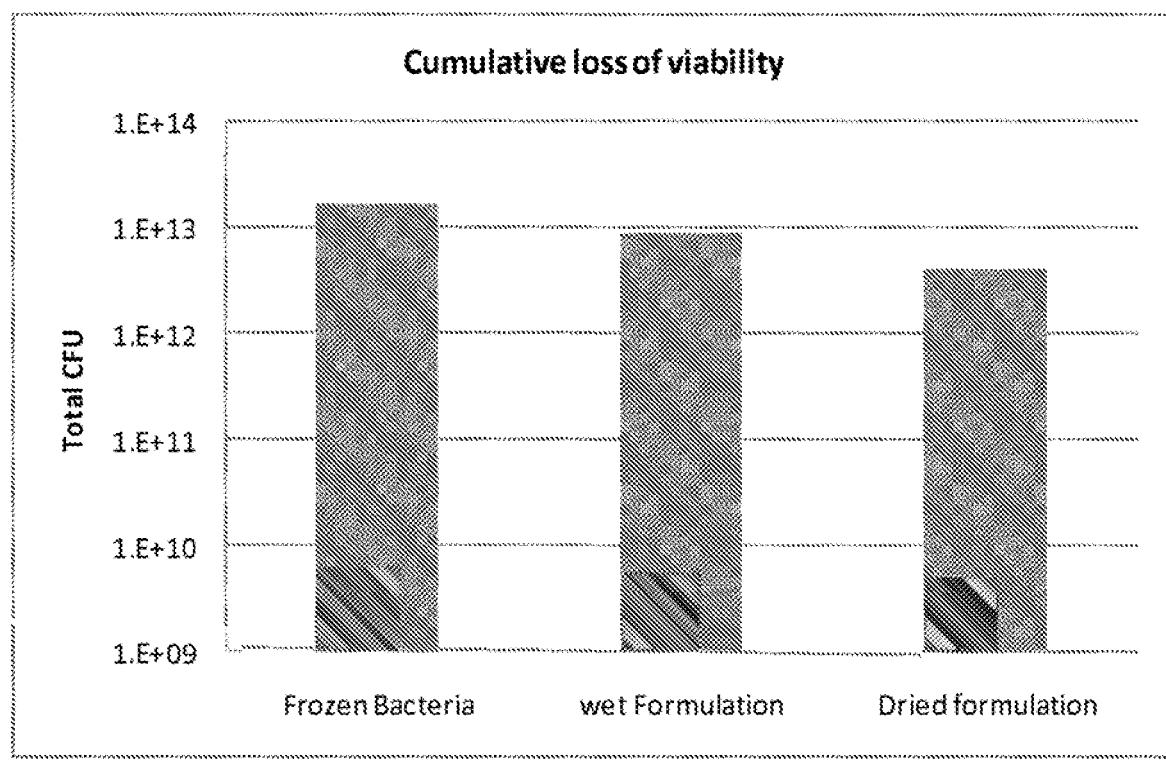
FIG. 2 shows the process temperatures and cumulative viability loss for a formulation process ending with Aw of 0.28 secondary drying step.

Single cell microorganisms have been shown to benefit particularly from the formulations and drying methods of the present invention. In one embodiment, the bioactive microorganism of the invention is probiotic bacteria. The formulation is prepared according to the compositions and methods of the invention including obtaining live probiotic bacteria in concentrated solution, paste, frozen beads or dry powder from. Mixing the probiotic bacteria under vacuum with a stabilizer agent and a protecting agent, cooling the viscous formulation to a temperature above its freezing temperature, applying sufficient vacuum pressure to maintain that pre-cooling temperature and supplying a heat source of 20° C. and above to facilitate water removal. Maintaining the pre-cooled temperature of the formulation can be by conduction of heat away from the formulation, and/or by loss of latent heat due to water evaporation. To further accelerate the drying process a secondary drying step is applied, at higher vacuum up to 0.1 Torr and at elevated temperature up to 70° C., to provide a final composition with water activity with an Aw of 0.3 or less. Such a composition can remain stable in storage conditions of 40° C. and 33% RH for 60 days or more (see FIG. 1). The specified processes of the invention have shown to result in the unexpected ability of the cells to retain their viability beyond that of established drying processes. The initial viability loss through the entire drying process according to the present invention was only 0.3 logs (see FIG. 2).

Formulations for Preparation of Stable Dry Powder Compositions

Figure 3:
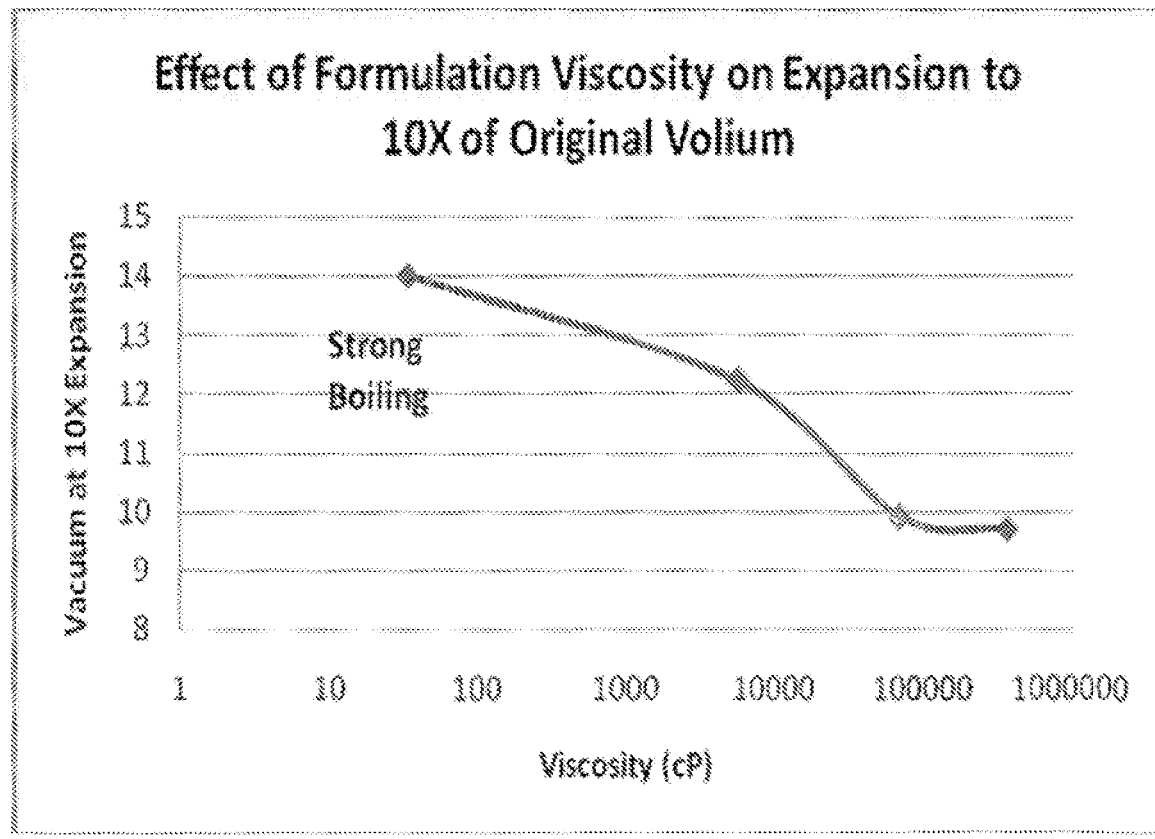
FIG. 3 shows the effect of alginate viscosity on the formulation expansion under vacuum.
Figure 4:
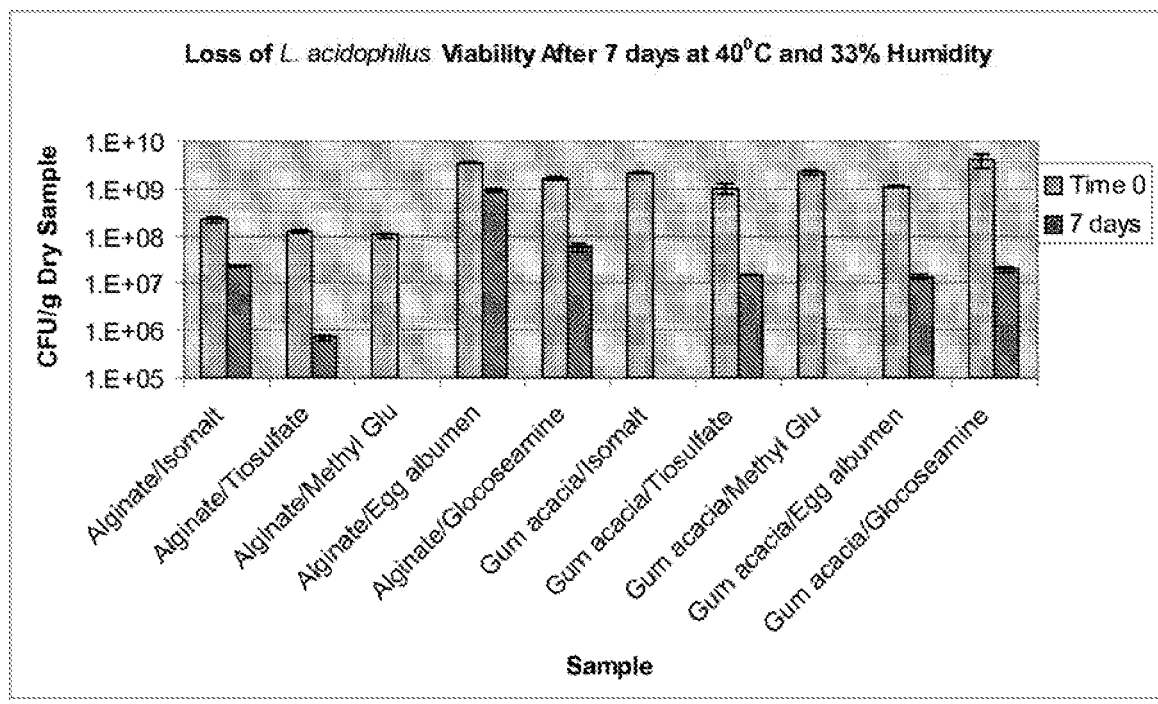
FIG. 4 shows the effect of different formulation stabilizers on storage stability.

The constituents to be mixed with the preferred microorganism or material for the preparation of dry powder compositions according to the invention, includes a stabilizer agent and protective agent. Such constituents, when mixed with the preferred bioactive microorganisms or material, can be processed according to methods of the invention to provide large quantities of stable dry compositions for storage and administration of said microorganisms. The formulation stabilizers can include a mixture of a polysaccharide and an oligosaccharide. The preferred polysaccharide, particularly for stabilizing live microorganisms, was alginate. Because it was surprisingly found that alginate is superior to other polysaccharides such as pectin and gum acacia in reducing the drying losses of sensitive biologicals such as probiotics (FIG. 4). It was also preferred because of its hydrogel forming characteristics with non-toxic metals at mild temperatures. Alginate was also found to effectively stabilize the formulation under vacuum, by providing appropriate viscosity to the formulation and allowing a controlled expansion of the formulation at a particular viscosity (FIG. 3).

Figure 5:
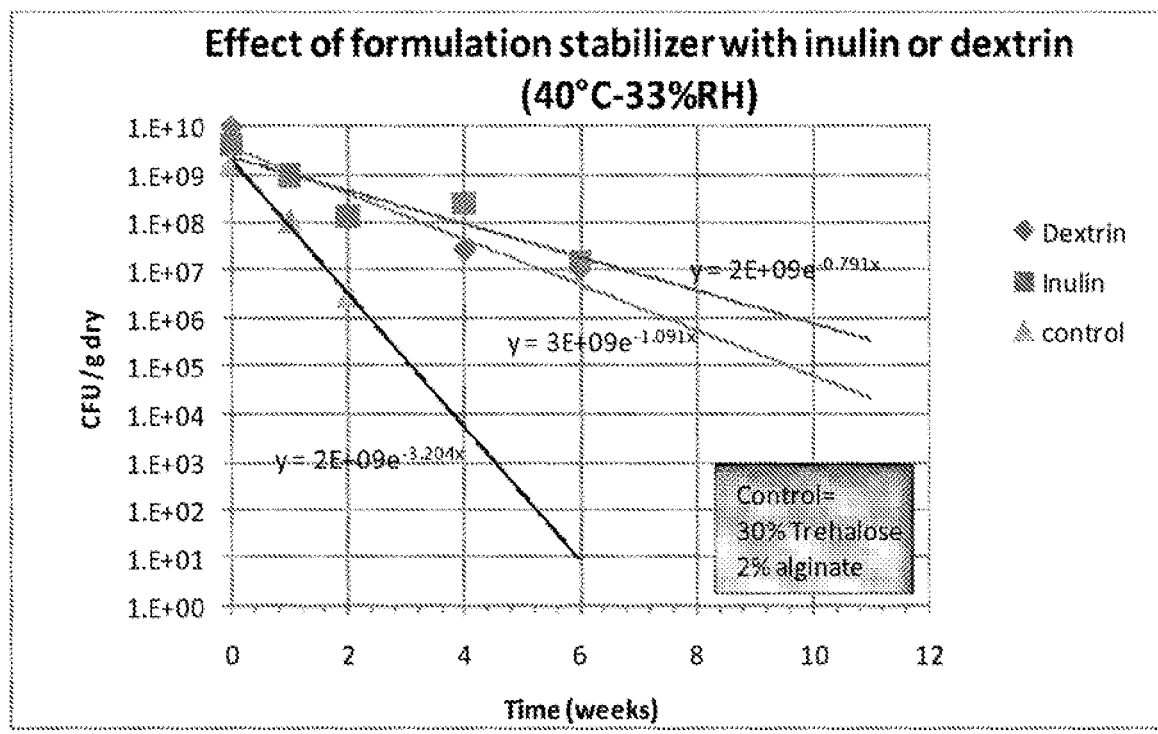
FIG. 5 shows the effect of different combinations of stabilizer agents on bacteria viability.

Combining an oligosaccharide with the alginate was also found to further contribute to the overall stability of the formulation. FIG. 5 shows the effect on storage stability of different combinations of alginate and oligosaccharides. A combination of alginate and inulin was the preferred combination in term of its long storage effect on the probiotic bacteria. In one embodiment of the invention, at least one of the formulation stabilizer agents is preferably a gum that can form a firm hydrogel by cross-linking with metal ions.

Protective agents of the invention can include various proteins, peptides, sugars, sugar alcohols and amino acids. The protective agent is preferably one that does not crystallize and/or destabilize the biologically active material in the formulation at freezing temperatures (e.g., −20° C.). It can be beneficial to include two or more different protective agents to inhibit the formation of crystals and stabilize the dried bioactive material formulation in storage conditions for long time periods.

The wet formulations can include a substantial amount of total solids (constituents minus the solvent, such as water). A major portion of the total solids can consist of the bioactive material, the stabilizer agent and the protective agent. For example, the bioactive material can be present in the formulation in a concentration ranging from about 2-50 weight percent, the stabilizer agent from about 1-20 weight percent, and the protective agent from about 20-80 weight percent. In another example, the stabilizer agent can be present in the formulation in a concentration ranging from about 0.5-10 weight percent, and the protective agent from about 10-40 weight percent. Preferably, the wet formulation should have solids content between about 5% and 80%; more preferably between about 30% to 60%. The viscosity of formulations of the invention are typically greater than 1000 centipoises (cP); more preferably, greater than 10,000 cP and less than 450,000; and most preferably greater than 30,000 cP and less than 100,000 cP.

The viscosity of formulations of the invention can be as high as 450,000 cP, provided that the protective agents are completely dissolved in the solution. Highly viscous and homogenous slurries containing substantial amount of total solids can be achieved at elevated temperature, depending on the thermo and osmo-sensitivity of the bioactive material. For example, live cells formulations containing 30-60% of total solids can be mixed at elevated temperature of about 35-40° C. and the mixing is carried out until all the protective agents are completely dissolved.

Methods of Preparing Stable Dry Formulations

Methods for preparing stable dry formulations for the preservation of bioactive microorganisms include, obtaining a live culture of a specific microorganism in a concentrated solution, paste, frozen beads or dry powder from (stabilized or otherwise). Preparation of a formulation by mixing, under vacuum, the bioactive microorganism or material with a stabilizer agent and a protecting agent in a solution, cooling the formulation to a temperature of no more than 10° C. above its freezing temperature, and drying the formulation by evaporating the moisture under reduced pressure while supplying heat to the formulation.

Figure 6:
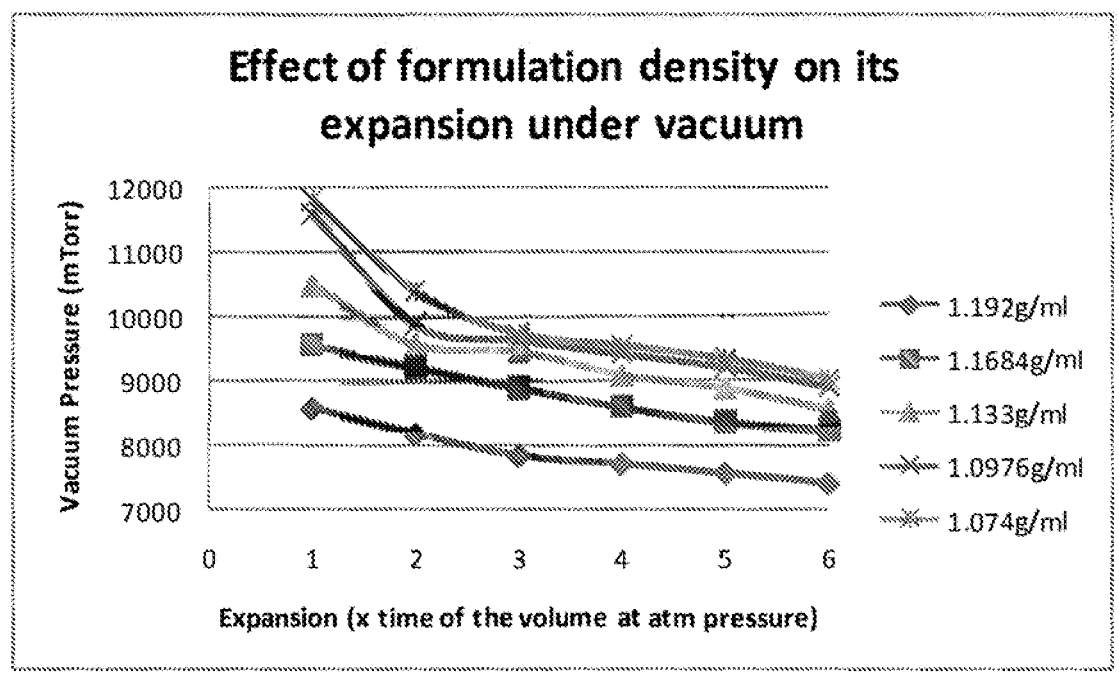
FIG. 6 shows the effect of the formulation density on expansion rate under vacuum.

In one embodiment, for example, a formulation comprising a bioactive microorganism or material, a formulation stabilizer agent, and a protecting agent are mixed to homogeneity, under mild vacuum of about 10-50 Torr, in a solution. FIG. 6 shows the effect of different densities of the formulation on its expansion under vacuum. The introduction of air during mixing of the formulation constituents in a solution results in excessive and un-controllable foaming even at relatively high vacuum pressure. The mixing under vacuum step according to the invention addresses this problem by eliminating the introduction of air or gas into the formulation solution, thereby eliminating excessive and uncontrolled foaming of the solution.

Figure 7:
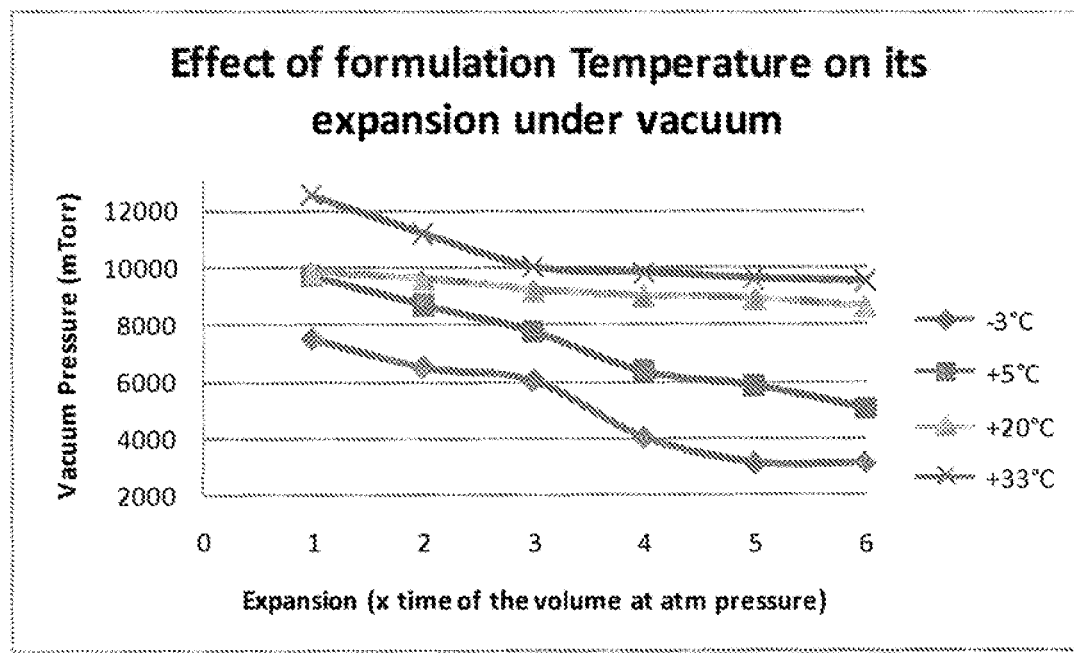
FIG. 7 shows the effect of the formulation pre-cooling temperature on expansion under vacuum.

The solution is then cooled down to a temperature above its freezing point (usually between −5° C. and +5° C.). FIG. 7 shows the effect of pre-cooling of the formulation solution on its expansion under vacuum pressure. It was surprisingly and unexpectedly found that boiling can be effectively eliminated even under a relatively higher vacuum pressure and formulation expansion is better controlled when the solution temperature is reduced to no more than 10° C. above its freezing temperature. As can be seen from FIG. 7, a vacuum pressure of 3 Torr can be applied without excessive foaming provided that the formulation is cooled to +5° C. and preferably to −3° C.

Figure 8:
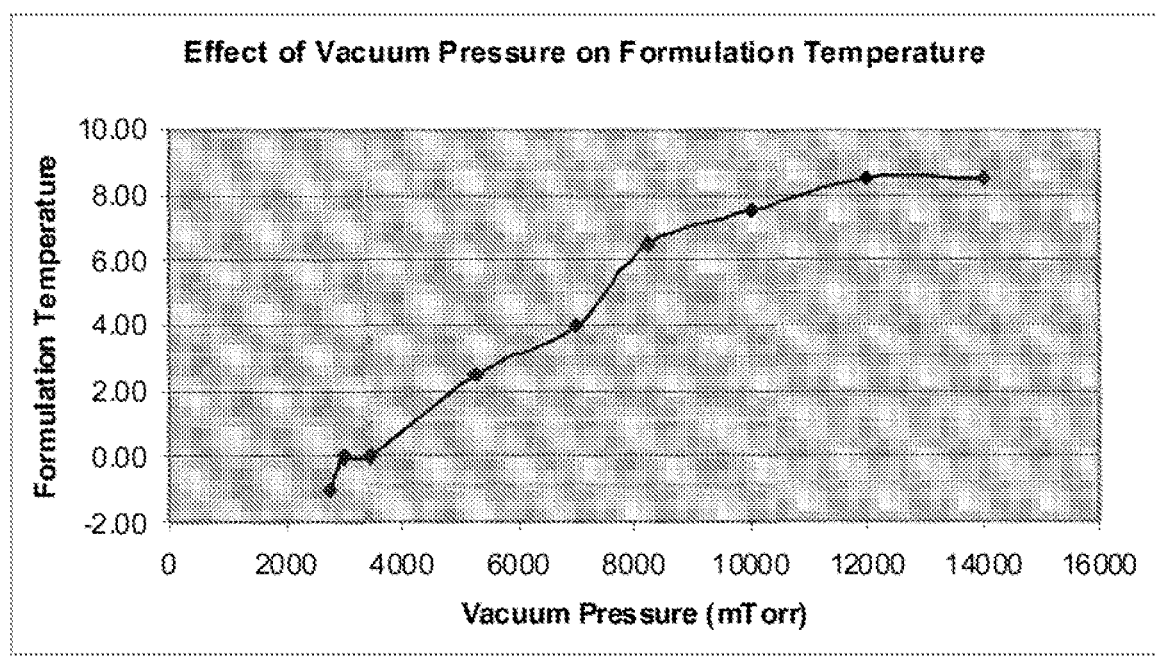
FIG. 8 shows the effect of the vacuum pressure on formulation temperature during primary drying step.

Once cooled, the formulation is then dried under sufficient vacuum (e.g., about 3 Torr) to maintain that pre-cooled temperature during the primary drying step. FIG. 8 shows the effect of the applied vacuum pressure on the temperature of the formulation solution. At relatively high vacuum pressure above 8 Torr, the formulation temperature increased to over 6° C. and will continued to rapidly increase toward the shelf or chamber temperature. At the same time, the solution will continue foaming and further expanding. This embodiment is distinguished from the prior art discussed above (see for example U.S. Pat. No. 6,534,087, where the applied vacuum pressure is between 3-7 Torr and even higher), in which a stronger vacuum pressure is applied (<3 Torr) while controlling the expansion of the formulation. This process results in a significantly faster drying rate (see FIG. 9) and enables a high loading capacity of the formulation. In this embodiment, excessive foaming and boiling is eliminated even under much lower vacuum pressures because the methods of the invention provide a) a specific composition with a controlled expansion under vacuum, b) a method that eliminates the introduction of air into the formulation during mixing and c) a substantial pre-cooling of the formulation.

Typical methods in the prior art involve extensive foaming and/or splattering and violent boiling that can be damaging to sensitive biologicals and cause difficulties for industrial scale up. Additionally, a complete and efficient degassing of viscous slurries is difficult and may require an extended period of time. These obstacles were resolved in the present invention by first carrying the entire mixing process under mild vacuum to eliminate the introduction of entrained gasses into the formulation in the first place. Any small amount of soluble gases that may remain in the formulation is then gently removed allowing the formulation to moderately expand under low vacuum. The additional pre-cooling step of the formulation to a temperature above its freezing temperature provides an added control of the expansion rate and thereby allows much higher loading capacity per drying area than was afforded according to the prior art. After the primary drying stage is complete, the stabilized dry formulation can be held at elevated secondary drying temperatures (up to 70° C.) and vacuum pressures of less than 0.2 Torr to complete drying of the formulation in a very short time.

Another embodiment of the invention provides methods to prepare hydrogel formulation compositions for preservation of bioactive microorganisms or materials. For example, a formulation containing a probiotic bacteria in a dry powder form, a stabilizer agent and a protective agent, are mixed in a solution, cross-linked to a hydrogel by adding metal ions or divalent cations and then dried under low vacuum and temperature as described above. The pre-cooled temperature of the formulation can be maintained by conduction of heat away from the formulation, and/or by loss of latent heat due to water evaporation.

In one particular embodiment of the invention, for example, the formulation includes a concentrated fresh or frozen or dry culture of live probiotic bacteria in a solution of 1 to 2.5% sodium alginate (preferably 1.5% sodium alginate), 1% to about 5% inulin (preferably 2.5% inulin), 20% to 60% trehalose (preferably 40% trehalose) and 3% to 15% casein hydrolysate (preferably 8% casein hydrolysate). The formulation is mixed under vacuum at a temperature slightly above the room temperature (typically between 25° C.-37° C.) until all the components are completely dissolved.

In one additional embodiment of the invention, all the ingredients are dissolved in the solution at elevated temperature, then the slurry is cooled down to a temperature between 0° C. to −5° C. and a dry powder of live microorganism is mixed in until all the components are completely dissolved. To facilitate the mixing of the dry live organism powder and to prevent clumping, a small amount of trehalose can be added to the dry powder (typically a mixture containing equal portions of dry powder and trehalose is sufficient.

The formulation slurry is spread on trays at loading capacity of about 200 g/sq ft and trays are placed on shelves in a freeze drier. The shelf temperature is adjusted to 0 to −5° C. (preferably 2° C.) and the slurry allowed to cool to that temperature. Vacuum pressure is then applied at 1 to 5 Torr (preferably 3 Torr) and shelf temperature increased to 20° to 45° C. (preferably 30° C.) for conductive heat transfer. The formulation temperature remained at about the temperature 0 to −5° C. during the primary evaporation step to prevent the sample from freezing. Secondary drying step at maximum vacuum of 0.1 Torr and shelf temperature of 40° C. is started when product temperature reached about +10° C. The entire drying process proceeds for about 4 hours at which time the product is harvested and water activity is at Aw−0.3 or less.

In another embodiment of the invention, the loaded trays are pre-cooled to −2° C. in a cold room then immediately loaded in a vacuum oven drier for radiant heat transfer. The primary and secondary drying steps are then applied as described above for conductive heat transfer.

Preparing the Formulation

Formulations of the invention can include fresh, frozen or dry live microorganisms formulated into a solution or suspension containing a formulation stabilizer agent and a protective agent. The formulation stabilizer and/or high concentration of protective agent can be dissolved into a heated aqueous solution with agitation before cooling and mixing with the bioactive microorganisms. The microorganisms, such as cultured virus or bacterium, can be concentrated and separated from culture media by centrifugation or filtration, then directly mixed into the formulation of the present invention, or added with conventional cryoprotectants dropped into liquid nitrogen and the small frozen beads stored at −80 C until mixed into the formulation. Alternatively, the frozen beads can be freeze dried, milled into a fine powder, packed in air tight bags and stored refrigerated until mixed in the formulation of the invention. In one embodiment of the present invention, the totality of the water in the formulation is provided in the liquid of the concentrated live organism and the live organism suspension is maintained at a temperature slightly above room temperature. The dry components of the formulation stabilizer agent and the protective agent are blended together and then slowly added to the warm suspension of the live organism. The formulation suspension is gently agitated under mild vacuum in a planetary mixer until all components are fully dispersed and uniform slurry is obtained.

In another embodiment of the present invention the bioactive microorganism is in the dry powder form and is premixed dry with formulation ingredients before the resulting dry mixture is added to water at a temperature slightly above room temperature.

The bioactive microorganism or material can provide any bioactivity, such as enzymatic activity, induction of immune responses, cellular multiplication, infection, inhibition of cell growth, stimulation of cell growth, therapeutic effects, pharmacologic effects, antimicrobial effects, and/or the like. The bioactive microorganism or material can be nonliving cells or liposomes useful as vaccines or delivery vehicles for therapeutic agents. Bioactive microorganism of the invention can be live viruses and live attenuated viruses and/or the like.

Formulation stabilizers provide structural stability to the formulation and/or physical and chemical protective benefits to the bioactive microorganisms. The stabilizers can provide thickening viscosity to the formulation and better control over its expansion properties under vacuum pressure and increased structural strength to the dried formulation compositions of the invention.

The protective agents can include a variety of proteins, protein hydrolysates, sugars, sugar alcohols and amino acids. For example, sugars such as sucrose or trehalose can physically surround the bioactive material to promote retention of molecular structure throughout the drying process and impart structural rigidity to the amorphous matrix in the dry state. The protective agent can replace water of hydration lost during drying, to prevent damage to cell membranes and denaturation of enzymes. Other functions of the protective agents can include protecting the bioactive material from exposure to damaging light, oxygen, oxidative agents and moisture. Most protective agents can be readily dissolved in a solution in amounts ranging from about 0.1 weight percent to about 60 weight percent.

Pre-Cooling the Formulation

Formulations of the invention can be pre-cooled before applying vacuum pressure of the drying process, to provide benefits such as a further thickening of the formulation slurry, a better control over the expansion of formulations under low vacuum pressure, stabilization of bioactive microorganism or material, and/or enhancing the penetration of formulation constituents through cell membranes. Cooling can be applied by any appropriate technique known in the art. For example, cooling can be by contact and conduction with cold surfaces, loss of latent heat, and/or the like. Typically, formulations are held in vessels or spread on metal trays and place in contact with a controlled temperature surface or a chamber where they equilibrate to the controlled temperature. Typically, the formulations of the invention can be pre-cooled to a temperature above its freezing temperature (e.g., between −5° C. and +5° C.).

Primary Drying of the Formulation

Typical processes for preservation of bioactive microorganisms such as, live or attenuated organisms include a combination of freezing and vacuum conditions that can result in membrane damage and denaturation of cell constituents. The prior art teaches the use of higher vacuum pressures (e.g., less than 100 Torr), addition of specific cryoprotective agents, concentrating steps to obtain thick solutions (syrup), and/or higher initial temperatures to prevent freezing. The use of formulations and process parameters of the present invention overcome these limitations and allow for higher loading capacity per drying area that significantly improves industrial output.

The formulation in the present invention is dried by evaporation. Removal of solvent (moisture) from the gaseous environment around the formulation can be driven by condensation or desiccation. Evaporation of solvent from the formulation can provide accelerated primary drying of the formulation under low vacuum pressure. The controlled expansion of the formulation accelerates the primary drying of the formulation by rapid transfer of solvent out of the formulation. The controlled expansion of the formulation is achieved by gentle degassing (not boiling) of the remaining dissolved gases when the drying vacuum is applied. Since it is desirable not to boil or excessively foam the formulation because the cavitations and shear forces associated with bubble formation during boiling and/or the formulation may spill out from containment or have a negative impact on the bioactive microorganism.

As primary drying proceeds, the formulation structure is stabilized. The heat supplied in the drying chamber compensates for the loss of latent heat caused by evaporation of solvent and the formulation temperature is maintained within 10° C. above its freezing temperature. At some point during the primary drying process, the rate of evaporation of solvent slows and the formulation temperature begins to increase due to superfluous supply of heat in the drying chamber. This point indicates the end of the primary drying step in this invention. As solvent is driven out from the formulation, the protective agents in solution become concentrated and thicker until it stops flowing as a liquid. The amorphous and/or glassy formulation preserves a stable formulation structure.

Secondary Drying

Secondary drying of the structurally stable formulation removes the remaining entrapped or bound moisture and provides a composition that is stable in storage for an extended period of time at ambient temperatures. Secondary drying involves the application of elevated temperatures and a strong vacuum for several hours to days. In preferred embodiments the time period necessary to complete the secondary drying step is double the time of the primary drying step. Preferably, the water activity of the formulation at the end of the secondary drying step is less than an Aw of 0.3. The drying temperature can range from about room temperature to about 70° C. A typical secondary drying process for many bioactive microorganisms can include raising the temperature from about 30° C. to about 40° C., and holding from about 30 minutes to about 24 hours (preferably from about 30 minutes to about 4 hours), to provide a stable dried formulation composition with water activity of less than an Aw of 0.3. In one particular embodiment of the secondary drying, the drying temperature is slowly raised from primary drying conditions at a rate that can further preserve the activity of live biologicals such as live microorganisms. A strong vacuum can be provided in the secondary drying process to accelerate the rate of water removal to lower residual moisture levels. The vacuum during the secondary drying can be less than 1 Torr and, preferably, less than about 0.2 Torr.

The drying methods of the invention result in a biologically active microorganism or bioactive material that is encased within an amorphous glassy matrix, thereby preventing the unfolding of proteins and significantly slowing molecular interactions or cross-reactivity, due to greatly reduced mobility of the compound and other molecules within the amorphous glassy composition. As long as the amorphous solid is at a temperature below its glass transition temperature and the residual moisture remains relatively low (i.e., below Aw of 0.3), the labile bioactive microorganism can remain relatively stable. It should be noted that achieving a glassy state is not a prerequisite for long term stability as some bioactive microorganisms or materials may fare better in a more crystalline state.

Preparation of Dry Powder

The dried formulation can be used en bloc, cut into desired shapes and sizes, or crushed and milled into a free flowing powder that provides easy downstream processing like wet or dry agglomeration, granulation, tabletting, compaction, pelletization or any other kind of delivery process. Processes for crushing, milling, grinding or pulverizing are well known in the art. For example, a hammer mill, an impact mill, a jet mill, a pin mill, a Wiley mill, or similar milling device can be used. The preferred particle size is less than about 1000 μm and preferably less than 500 μm.

The compositions and methods described herein preserve the biological activity of the encased biologically active microorganism or bioactive materials. For example, the compositions are tested for stability by subjecting them at elevated temperature (e.g., 40° C.) and high humidity (e.g. 33% RH) and measuring the biological activity of the formulations. As an example for live probiotic bacteria, results of these studies demonstrate that the bacteria formulated in these formulations are stable for at least 60 days (see FIG. 1). Stability is defined as time for one log CFU/g potency loss. Such formulations are stable even when high concentrations of the biologically active material are used. Thus, these formulations are advantageous in that they may be shipped and stored at temperatures at or above room temperature for long periods of time.

EXAMPLES

The following examples are offered to illustrate, but not to limit the claimed invention.

Example 1

Preparation of Dry Premixed Formulation:

Several formulation premixes were prepared according to Table 1. Trehalose was obtained from Cargill Minneapolis, Minn. Soy protein isolate was obtained from Fearn Natural Foods, Mequon, Wis. Whey protein Concentrate was obtained from Agri-Mark Inc., Middlebury, Vt. Casein hydrolysate was obtained from Marcor, Carlstadt, N.J., and sodium alginate from ISP Corp., Wayne, N.J. All ingredients were combined together and uniformly mixed (Table 1).

TABLE 1

Formulations Premix composition (weight percent)

| Constituent | Soy premix | Whey premix | Protein hydrolysate premix |
|---|---|---|---|
| Sodium Alginate | 3.0 | 3.0 | 3.0 |
| Inulin | 5.0 | 5.0 | 5.0 |
| Trehalose | 75.3 | 75.3 | 75.3 |
| Soy protein Isolate | 14 | — | — |
| Whey protein concentrate | — | 14 | — |
| Casein Hydrolysate | 2.7 | 2.7 | 16.7 |

Example 2

Stable Dry Powder Containing Probiotic Bacteria:

*Lactobacillus Acidophilus* (100 g frozen concentrate from a lab fermentation harvest) was thawed at 37° C. Protein hydrolysate premix (100 g, Table 1) was slowly added to the thawed slurry of probiotic bacteria in a jacketed dual planetary mixer (DPM, 1 qt, Ross Engineering, Inc. Savannah, Ga.). Mixing was carried out under mild vacuum (25 Torr) at 40 RPM and 37° C. for 10 minutes. The homogenous slurry was evenly spread on a tray at a loading capacity of 200 g/sq ft and the tray placed on a shelf in a freeze drier (Model 25 SRC, Virtis, Gardiner, N.Y.). Shelf temperature was set above the freezing temperature of the slurry at −5° C. to cool, but not to freeze, the slurry. Vacuum pressure (3 Torr) was applied when the formulation temperature reached about −1° C. The slurry starts to gently degas when vacuum reached about 7 Torr. When the vacuum reached 3 Torr, the shelf temperature was increased to 50° C. The formulation temperature remained at about −1° C. to about +5° C. during the first 50 minutes of primary drying step. Once the formulation temperature increased to +10° C., the secondary drying step was initiated. Maximum vacuum of 0.1 Torr was applied while still shelf temperature continued to maintain at 50° C. Secondary drying step was continued for additional 100 minutes, at which point the drying process was terminated and the dry formula removed from the freeze drier. The water activity of the dry formulation at this point was Aw=0.23 as measured by a Hygropalm Aw1 instrument (Rotonic Instrument Corp., Huntington, N.Y.).

Figure 9:
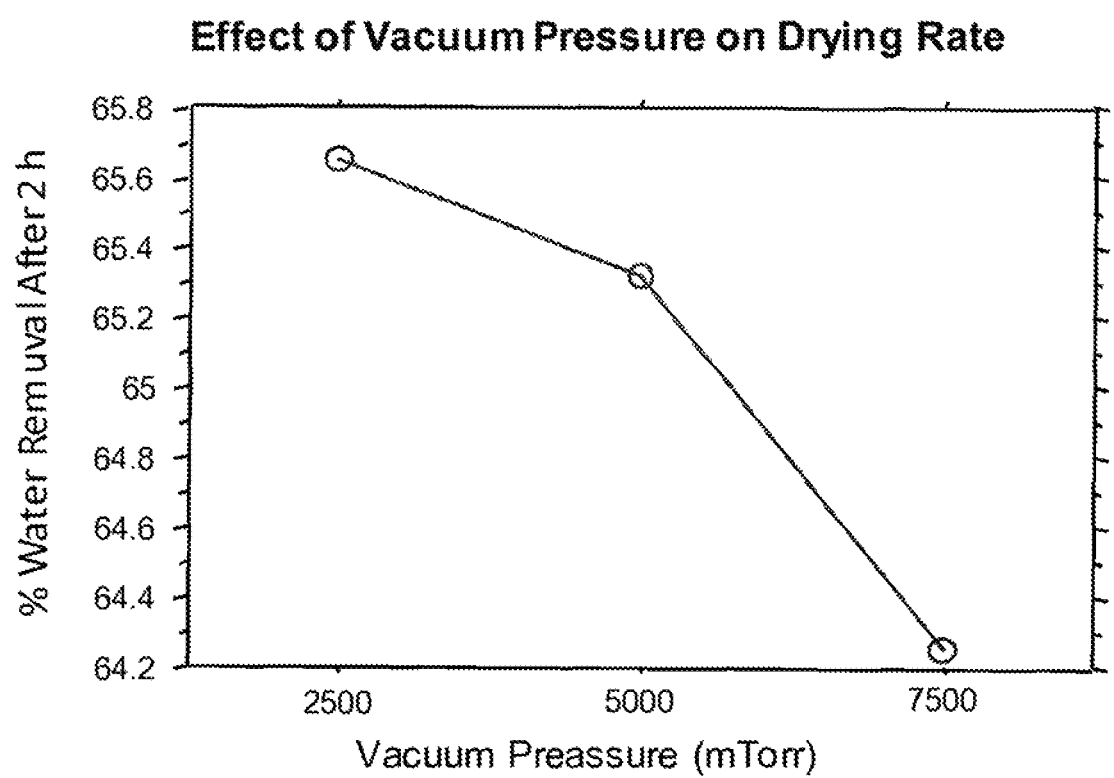
FIG. 9 shows the effect of the vacuum pressure on drying rate of the formulation.

The viability losses during formulation, preparation, and drying processes are presented in FIG. 9. Viability losses during formulation preparation were 0.26 logs and 0.34 logs during the drying process for a total cumulative loss of 0.6 logs.

Figure 10:
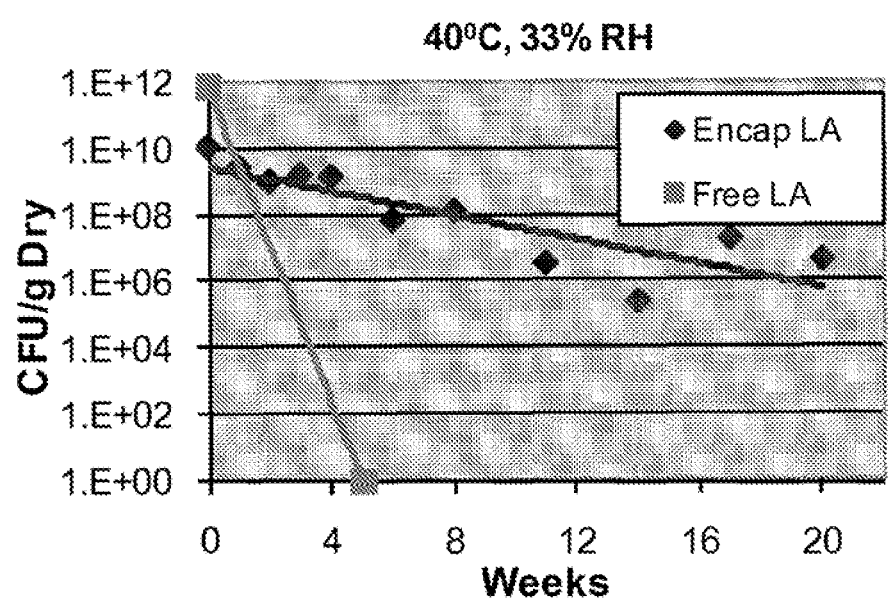
FIG. 10 shows the stability of the probiotic bacteria, *L. acidophilus* dried with the formulation and method of the invention under storage at 37° C. and 33% relative humidity.

FIG. 10 shows the storage stability of the dry formulation under accelerated storage conditions of 37° C. and 33% RH. After four weeks at these storage conditions, the viability loss of the probiotic bacteria stabilized in the formulation of the invention was only 0.8 logs.

Example 3

Figure 11:
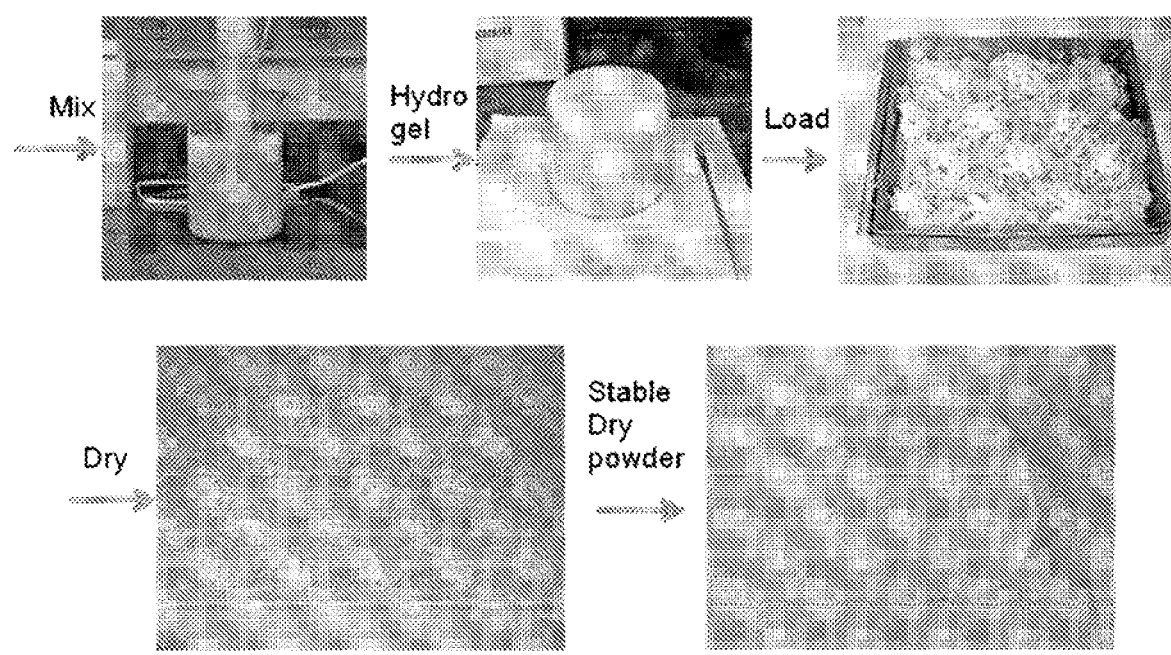
FIG. 11 shows a flow chart of the method of production stable dry formulation from hydrogel formulation according to the invention.

Preparation of a Hydrogel Formulation:

Concentrated probiotic slurry was prepared according to Example 2 but using the whey protein premix of Table 1. To this slurry, 0.5 g of dibasic calcium phosphate was added, followed by 0.5 g of gluconolactone. The slurry was allowed to harden at room temperature over the next 2 hours to form a solid hydrogel. The firm gel was sliced to thin and long threads, using a commercially available slicer/shredder. The thin threads were loaded on a tray at a loading capacity of 200 g/sq ft and placed in a freeze drier for drying as described in Example 2. Four hours after establishing maximum vacuum of 0.1 Torr, the dried product was taken out of the freeze drier. The water activity (Aw) of the formulation was 0.05 (Measured by HygroPalm Aw1, Rotonic Huntington, N.Y.). The dry formulation was further ground to fine powder using standard hammer milling equipment and sieved through 50-250 micron screens. FIG. 11 present a flow chart of the method of production stable dry formulation from a hydrogel formulation according to the invention.

Example 4

Preparation of Probiotic Pet Food:

A commercially available pelleted pet food for dogs is dried in a convection oven to a water activity of 0.1, and then coated with the stable probiotic dry formulation prepared as described in Example 3. The dry pellets are sprayed with about 5% of fat-based moisture barrier (a mixture of 40% chicken fat, 40% cocoa butter and 20% beeswax), mixed in a drum tumbler with the dry powder formulation (usually 0.1-0.5% of total pet food that provides a dosage of $10.\sup8$ CFU/g), and finally sprayed with additional coat of the fat-based moisture barrier. The total amount of coating is about 15% (of the pet food). Coating time is about 30 min.

Example 5

Preparation of Fish Feed with Several Probiotic Microorganisms:

Pelleted feed for fish according to the present invention was prepared with a mixture of several probiotics. A stable dry probiotic formulation containing a mixture of *L. rhamnosus, L. acidophilus* and *Bifidobacterium lactis* was prepared as described in Example 2. A commercially available starter feed for salmon (Zeigler Bros., Gardners, Pa.) was first dried in a convection oven to a water activity of 0.1, and then coated with the probiotics formulation in a drum tumbler. The pellets (100 g) were first sprayed with about 5% by weight of fat-based moisture barrier (a mixture of 40% fish oil, 40% cocoa butter and 20% beeswax), then mixed with 1 g of the stable dry probiotic formulation (to attain a dosage of $10^7$ cfu/g feed), and finally sprayed with additional coat of the fat-based moisture barrier. The total amount of coating was about 10% of the fish feed.

Example 6

An Infant Formula Containing the Dry Formulation of the Present Invention:

A stable dry formulation containing *Lactobacillus GG* (Valio Corp, Finland) is prepared according to Example 2 followed by a sieving into two particle size groups (above 50 pm and below 150 μm). An infant formula is prepared by mixing 99 g of an infant formula from Mead Johnson (Evansville, Ill.) with 0.1 g of the small size particles (below 50 μm). The final product contains about $10^8$ cfu of *Lactobacillus* GG per 100 g infant formula.

Example 7

Stable Dry Powder Containing an Enzyme:

A hydrogel formula containing 40 weight percent of proteases from Novozymes (Denmark) is prepared by mixing, under mild vacuum, 60 g of protein hydrolysate formulation premix (Table 1) and 40 g of the proteases in 100 g of water solution. The wet formulation is dried in a vacuum oven at a drying temperature of 50° C. For determination of loading and storage stability of the dried formula: a dry sample is accurately weighed (<100 mg) in a microcentrifuge tube. 200 μl of dimethyl sulfoxide (DMSO) is added. The formulation is dissolved in the DMSO buffer by vortexing. To this sample, 0.8 ml of a solution containing 0.05 N NaOH, 0.5% SDS and 0.075 M Citric acid (trisodium salt) is added. The tubes are sonicated for 10 min at 45° C., followed by a brief centrifugation at 5,000 rpm for 10 min. Aliquots of the clear DMSO/NaOH/SDS/Citrate solution are taken into wells of a microplate and analyzed for protein content using the Bradford assay method. The storage stability of the stable enzyme formulation is significantly higher than a dry enzyme without the formulation of the present invention.

Example 8

Stable Dry Powder Containing Vitamin A:

A hydrogel formula containing 50 weight percent of Vitamin A (BASF Corp., Florham Park, N.J.) is prepared by mixing, under 25 Torr vacuum, 50 g of soy protein formulation premix (Table 1) and 50 g of vitamin A powder in 100 g of water solution. The wet formulation is pre-cooled to −5° C., then spread on trays at a loading capacity of 200 g/sq ft and dried in a vacuum oven at an initial vacuum pressure of 3 Torr and temperature of 70° C., followed by a maximum vacuum step of 0.2 Torr at 70° C. once the formulation temperature reached to 5° C.

Example 9

Preparation of Invasive Species Bait:

Pelleted bait for specifically targeted invasive species according to the present invention is prepared containing a pesticide. The whey protein premix of Table 1 is added to 200 gm of water. To this solution is added 90 gm of rotenone and 0.5 gm of calcium phosphate dibasic, followed by 0.5 gm of gluconolactone. The slurry is allowed to harden at room temperature over 2 hours. The firm gel is sliced to thin and long threads through a slicer/shredder. The thin threads are loaded on a tray and placed in a vacuum oven dryer. Drying is stopped after achieving a water activity of 0.10. The dry formulation is ground to the appropriate size distribution for the bait size specification for the specific species targeted.

Example 10

Preparation of a Protected Pesticide in a Water-Soluble Formulation:

A protected soluble granular formulation of a pesticide that would otherwise be subject to decomposition by other ingredients in a formulation during storage is prepared by the process of the present invention. The soy protein premix of Table 1 is added to 200 g of water. To this solution is added 80 g of a dry formulation of a sensitive formulated pesticide. The slurry is transferred to a vacuum oven dryer and dried to a water activity of 0.1. The dry formulation is milled to the desired size and packaged.

Example 11

Preparation of a Protected Pesticide in a Water Insoluble Formulation:

A protected insoluble granular formulation of a pesticide that would otherwise be subject to decomposition by other ingredients in a formulation during storage is prepared with the formulation and the method of the present invention. The soy protein premix of Table 1 is added to 200 g water. To this solution is added 90 g of a dry formulation of a sensitive pesticide and 0.5 g of calcium phosphate dibasic, followed by 0.55 g of gluconolactone. The slurry is allowed to harden at room temperature over 2 hours, and then sliced to thin, long threads through a slicer/shredder. The thin threads are loaded on trays and dried in a vacuum oven dryer to reach a water activity of 0.1. The dry formulation is further milled to the desired size distribution and packaged.

Example 12

Ten (10) grams of dry *Lactobacillus rhamnosus* GG is mixed with 100 g of the protein hydrolisate premix of Example 1 (table 1). This dry mixture is slowly added to 100 gm of deionized water at 35° C. in a jacketed dual planetary mixer, and mixed for 10 minutes at 40 rpm. The homogeneous slurry is evenly spread on a tray at a loading capacity of 100 gm/sq ft, and the tray is placed on a shelf in a freeze dryer (Model 25 SRC, Virtis, Gardiner, N.Y.). The shelf temperature is set at 5° C. to cool the slurry. Vacuum is applied to reduce the pressure to 3 Torr, at which time the shelf temperature is raised to 30° C. After 2 hours the pressure is reduced further to 150 milliTorr with the shelf temperature still held at 30° C. Drying is continued for an additional 3 hours at which point the product temperature has risen to within 2° C. of the shelf temperature. The dried product is then removed from the freeze dryer and the water activity of the dry formulation at this point is measured by a Hygropalm Aw1 instrument. Viability losses during formulation, preparation and drying processes are measured and recorded. Storage stability testing of the dry formulation is conducted under accelerated storage conditions of 32° C. and 20% RH.

Results for the trial at 30° C., and also for one repeated at 40 C are shown below

| Water Activity after drying | 0.25 | 0.26 |
|---|---|---|
| Losses during drying | 0.5 log | 0.7 log |
| Losses during storage | 0.4 log | 0.7 log |

Example 13

Twenty (20) grams of dry *Lactobacillus rhamnosus* GG is mixed with 100 g whey protein premix Example 1. This dry mixture is slowly added to 100 gm of deionized water at 35° C. in a jacketed dual planetary mixer, and mixed for 10 minutes at 40 rpm. The homogeneous slurry is evenly spread on a tray at a loading capacity of 100 gm/sq ft, and the tray is placed on a shelf in a freeze dryer (Model 25 SRC, Virtis, Gardiner, N.Y.). The shelf temperature is set at 5° C. to cool the slurry. Vacuum is applied to reduce the pressure to 3 Torr, at which time the shelf temperature is raised to 30° C. After 2 hours the pressure is reduced further to 150 milliTorr with the shelf temperature still held at 30° C. Drying is continued for an additional 3 hours at which point the product temperature has risen to within 2° C. of the shelf temperature. The dried product is then removed from the freeze dryer and the water activity of the dry formulation at this point is measured by a Hygropalm Aw1 instrument. Viability losses during formulation, preparation and drying processes are measured and recorded.

Storage stability testing of the dry formulation is conducted under accelerated storage conditions of 32° C. and 20% RH.

Results for the trial at 30° C. and also for one repeated, but run at 40° C. are shown below:

| Water Activity after drying | 0.23 | 0.26 |
|---|---|---|
| Losses during drying | 0.6 log | 0.7 log |
| Losses during storage | 0.8 log | 0.7 log |

Example 14

Ten (10) grams of dry *Lactobacillus acidophilis* are mixed with 10 gms of trehalose and briefly set aside while 65.3 gm of trehalose, 3 gm of sodium alginate, 5 gm of inulin and 16.7 gm of whey hydrolysate are mixed together as a dry powder and slowly added to 100 gm of deionized water at 35° C. in a jacketed dual planetary mixer, and mixed for 5 minutes at 40 rpm. To this slurry is added the *Lactobacillus acidophilis* and trehalose dry premix, and the mixing is continued for an additional 5 minutes at 35° C. The homogeneous slurry is evenly spread on a tray at a loading capacity of 100 gm/sq ft, and the tray is placed on a shelf in a freeze dryer (Model 25 SRC, Virtis, Gardiner, N.Y.). The shelf temperature is set at 5° C. to cool the slurry. Vacuum is applied to reduce the pressure to 3 Torr, at which time the shelf temperature is raised to 30° C. After 2 hours the pressure is reduced further to 150 milliTorr with the shelf temperature still held at 30° C. Drying is continued for an additional 3 hours at which point the product temperature has risen to within 2° C. of the shelf temperature. The dried product is removed from the freeze dryer and the water activity of the dry formulation at this point is measured using a Hygropalm Aw1 instrument. Viability losses during formulation, preparation and drying processes are measured and recorded. Storage stability testing of the dry formulation is conducted under accelerated storage conditions of 32° C. and 20% RH. Results for the trial where the dryer is maintained at 30° C. and compared to those where the dryer is maintained at 50° C. are shown in Table below.

| Water Activity after drying | 0.23 | 0.26 |
|---|---|---|
| Losses during drying | 0.6 log | 0.7 log |
| Losses during storage | 0.8 log | 0.9 log |

Example 15

Ten (10) grams of dry *Lactobacillus acidophilis* are mixed with 10 gms of trehalose and briefly set aside while 65.3 gm of trehalose, 3 gm of sodium alginate, 5 gm of inulin and 16.7 gm of whey hydrolysate are mixed together as a dry powder and slowly added to 100 gm of deionized water at 50° C. in a jacketed dual planetary mixer, and mixed for 5 minutes at 40 rpm. The slurry is cooled down to 4° C. To this cooled slurry is added the *Lactobacillus acidophilis* and trehalose premix, and the mixing is continued for an additional 5 minutes at 4° C. The homogeneous slurry is evenly spread on a tray at a loading capacity of 100 gm/sq ft, and the tray is placed on a shelf in a freeze dryer (Model 25 SRC, Virtis, Gardiner, N.Y.). The shelf temperature is set at 5° C. to maintain the temperature of the cool slurry. Vacuum is applied to reduce the pressure to 3 Torr, at which time the shelf temperature is raised to 30° C. After 2 hours the pressure is reduced further to 150 milliTorr with the shelf temperature still held at 30° C. Drying is continued for an additional 3 hours at which point the product temperature has risen to within 2° C. of the shelf temperature. The dried product is removed from the freeze dryer. The water activity of the dry formulation at this point is Aw=0.23 as measured by a Hygropalm Aw1 instrument. Viability losses during formulation, preparation and drying processes total 0.6 logs.

Example 16

One hundred (100) gram of soy premix is slowly added to 100 gm of deionized water at 35° C. in a jacketed dual planetary mixer, and mixed for 10 minutes at 40 rpm. Ten (10) grams of dry *Bifidobacterium lactis* Bb-12 is added slowly with mixing at 20 rpm, and the slurry mixed for an additional 5 minutes. The homogeneous slurry is evenly spread on a tray at a loading capacity of 100 gm/sq ft, and the tray is placed on a shelf in a freeze dryer (Model 25 SRC, Virtis, Gardiner, N.Y.). The shelf temperature is set at 5° C. to cool the slurry. Vacuum is applied to reduce the pressure to 3 Torr, at which time the shelf temperature is raised to 30° C. After 2 hours the pressure is reduced further to 150 milliTorr with the shelf temperature still held at 30° C. Drying is continued for an additional 3 hours at which point the product temperature has risen to within 2° C. of the shelf temperature. The dried product is removed from the freeze dryer and the water activity of the dry formulation at this point is Aw=0.26 as measured by a Hygropalm Aw1 instrument. Viability losses during formulation, preparation and drying processes total 0.7 logs.

Storage stability testing of the dry formulation under accelerated storage conditions of 32° C. and 20% RH show a viability loss of the stabilized probiotic bacteria in the formulation of the invention to be only 0.7 logs after four weeks.

Example 17

The same parameters as Example #1, except the mixing done in the Ross mixer is under 25 inches of vacuum to give a slurry density of 1.2 gm/cc. The water activity of the dry formulation at this point is Aw=0.26 as measured by a Hygropalm Aw1 instrument. Viability losses during formulation, preparation and drying processes total 0.5 logs.

Storage stability testing of the dry formulation under accelerated storage conditions of 32° C. and 20% RH show a viability loss of the stabilized probiotic bacteria in the formulation of the invention to be only 0.7 logs after four weeks.

Example 18

One hundred (100) grams of a fresh liquid concentrate of LGG bacteria (containing 10% solids and the rest water) is added to a jacketed dual planetary mixer and warmed to 35° C. To this is slowly added 100 g of whey premix (Table 1). The resulting slurry is mixed for 10 minutes at 40 rpm. The homogeneous slurry is evenly spread on a tray at a loading capacity of 100 gm/sq ft, and the tray is placed on a shelf in a freeze dryer (Model 25 SRC, Virtis, Gardiner, N.Y.). The shelf temperature is set at 5° C. to cool the slurry. Vacuum is applied to reduce the pressure to 3 Torr, at which time the shelf temperature was raised to 30° C. After 2 hours the pressure is reduced further to 150 milliTorr with the shelf temperature still held at 30° C. Drying is continued for an additional 3 hours at which point the product temperature has risen to within 2° C. of the shelf temperature. The dried product is removed from the freeze dryer. The water activity of the dry formulation at this point is Aw=0.25 as measured by a Hygropalm Aw1 instrument. Viability losses during formulation, preparation and drying processes total 0.5 logs. Storage stability testing of the dry formulation under accelerated storage conditions of 32° C. and 20% RH show a viability loss of the stabilized probiotic bacteria in the formulation of the invention to be only 0.4 logs after four weeks.

Example 19

*Lactobacillus rhamnosus* GG (LGG) One hundred (100) grams of unthawed, frozen concentrate and 100 g of protein hydrolysate premix were added to a jacketed dual planetary mixer (DPM, 1 pt, Ross Engineering, Inc., Savannah, Ga.). This process can also be done by thawing the frozen concentrate first. Mixing was carried out at 40 RPM and 37° C. for 10 minutes. The homogeneous slurry was measured for viscosity (Brookfield viscometer, Model #LVDVE115, Brookfield Engineering Laboratories, Inc.), and then evenly spread on a tray at a loading capacity of 100 g/sq ft. Viscosity Parameters for high viscosity ranges were: 300 g sample in a 400 mL Pyrex beaker, 33-37 C, Spindle #64, 1.0 RPM speed, operated without a guard-leg. The tray was then loaded into a −4° C. refrigerator for cooling for 30 min. After cooling, the drying began using a freeze drier (Model 25 SRC, Virtis, Gardiner, N.Y.) with a shelf temperature set at 30° C. throughout, and 2800 mTorr of pressure for at least 2.5 hours. After at least 2.5 hours, the pressure was decreased to 100 mTorr for at least another 2.5 hours. This experiment was repeated with two different batches of LGG fermentate, and included washing of one batch with 3% DMV and reconstitution with de-ionized water prior to adding the hydrolysate premix.

| Sample | CFU/g of final product | Losses during drying | Viscosity of slurry (cP) |
| --- | --- | --- | --- |
| LGG Batch # 1 | $2.20 \times 10^{+10}$ | 0.61 | 410,000 |
| LGG Batch # 2 | $7.00 \times 10^{+10}$ | 0.48 | N/A |
| Washed LGG Batch # 2 | $1.38 \times 10^{+11}$ | 0.21 | 319,000 |

Viscosity Parameters for medium viscosity ranges were: 300 g sample in a 400 mL Pyrex beaker, 33-37° C., Spindle #64, 5.0 RPM speed, operated without a guard-leg.

| Sample | CFU/g of final product | Losses during drying | Viscosity of slurry (cP) |
| --- | --- | --- | --- |
| LGG Batch # 4 | $1.39 \times 10^{+11}$ | 0.18 | 58,100 |
| Washed LGG Batch # 4 | $1.31 \times 10^{+11}$ | 0.23 | 36,200 |

Example 20

*Lactobacillus rhamnosus* GG (LGG) One hundred (100) grams of frozen concentrate was thawed at 37° C. and added to a jacketed dual planetary mixer (DPM, 1 pt, Ross Engineering, Inc., Savannah, Ga.). To it, 100 g of protein hydrolysate premix was added. Unthawed frozen concentrate may also be used. Mixing was carried out at 40 RPM and 37° C. for 10 minutes, and then the slurry was evenly spread onto trays at a loading capacity of 100 g/sq ft. The trays were then loaded into a −4° C. refrigerator for cooling for 30 min. After cooling, the drying begins using a freeze drier (Model 25 SRC, Virtis, Gardiner, N.Y.) with a shelf temperature set at 30° C. throughout, and 2800 mTorr of pressure for at least 2.5 hours. After at least 2.5 hours, the pressure was decreased to 100 mTorr for at least another 2.5 hours. This same process was applied to 10 g of dried (powdered) LGG material, which was mixed into 100 g of protein hydrolysate. This dry mixture was then slowly added to 90 g of de-ionized water in the jacketed dual planetary mixer.

| Sample | Losses during drying (logs) |
| --- | --- |
| Dry LGG/MM final product | 1.26 |
| Frozen LGG concentrate/MM final product | 1.46 |

Example 21

Stable Dry Powder Containing Enzyme:

Forty (40) gram of proteolitic enzyme (Novozymes, Denmark) in the form of dry powder is mixed with 60 g of soy premix (Table 1). This dry mixture is slowly added to 100 g of deionized water at 35° C. in a jacketed dual planetary mixer, and mixed for 10 minutes at 40 rpm. The homogeneous slurry is evenly spread on a tray at a loading capacity of 100 gm/sq ft, and the tray placed on a shelf in a freeze dryer (Model 25 SRC, Virtis, Gardiner, N.Y.). The shelf temperature is set at 5° C. to cool the slurry. Vacuum is applied to reduce the pressure to 3 Torr, at which time the shelf temperature is raised to 60° C. After 1 hour the pressure is reduced further to 150 milliTorr with the shelf temperature still held at 60° C. Drying is continued for an additional 1 hour at which point the product temperature had risen to within 2° C. of the shelf temperature. The dried product is removed from the freeze dryer. For determination of loading and storage stability of the dried formula: the dry sample is accurately weighed (<100 mg) in a microcentrifuge tube and 200 μg of dimethyl sulfoxide (DMSO) is added. The formulation is dissolved in the DMSO buffer by vortexing. To this sample, 0.8 ml of a solution containing 0.05N NaOH, 0.5% SDS and 0.075M Citric acid (trisodium salt) is added. The tubes are sonicated for 10 min at 45° C., followed by a brief centrifugation at 5,000 rpm for 10 min. Aliquots of the clear DMSO/NaOH/SDS/Citrate solution are taken into wells of a microplate and analyzed for protein content using the Bradford assay method. The storage stability of the stable enzyme formulation is significantly higher than a dry enzyme without the formulation of the present invention.

REFERENCES

The contents of the references cited herein are incorporated by reference herein for all purposes.

U.S. Pat. No. 6,964,771 Method for stably incorporating substances within dry, foamed glass matrices. September 1997. Roser et al.

U.S. Pat. No. 5,766,520 Preservation by formulation formation. June 1998. Bronshtein U.S. Pat. No. 6,534,087 Process for preparing a pharmaceutical composition. June 2001. Busson and Schroeder.

U.S. Pat. No. 6,884,866 Bulk drying and the effects of inducing bubble nucleation. April 2005. Bronshtein.

U.S. Pat. No. 7,153,472 Preservation and formulation of living cells for storage and delivery in hydrophobic carriers December, 2006 Bronshtein 20080229609 Preservation by Vaporization. June 2005. Bronshtein U.S. Pat. No. 6,306,345 Industrial scale barrier technology for preservation of sensitive biological materials at ambient temperatures October 2001. Bronshtein et al.

Morgan, C. A., Herman, N., White, P. A., Vesey, G. 2006. Preservation of micro-organisms by drying; a review. J. Microbiol. Methods. 66(2):183-93.

Capela, P., Hay, T. K. C., & Shah, N. P. 2006. Effect of cryoprotectants, prebiotics and microencapsulation on survival of probiotic organisms in yoghurt and freeze-dried yoghurt. Food Research International, 39(3) 203-211).

Annear, 1962. The Preservation of *Leptospires* by Drying From the Liquid State, J. Gen. Microbiol., 27:341-343.

That which is claimed is:

1. A dry composition comprising a bioactive microorganism embedded in a matrix, said matrix comprising 3% sodium alginate, 5% inulin, 75.3% trehalose, and 16.7% protein hydrolysate, wherein the % is by weight of the matrix.

2. The composition of claim 1, wherein the bioactive microorganism is present at 2-50% of the total weight of the dry composition.

3. The composition of claim 1, wherein the bioactive microorganism is a virus, a probiotic, a yeast, or an algae.

4. The composition of claim 1, wherein the bioactive microorganism comprises *L. rhamnosus*, wherein the composition exhibits less than one log loss of Colony Forming Units per gram (CFU/gram) for at least two weeks at 40° C. and 33% relative humidity.

* * * * *

UNITED STATES PATENT AND TRADEMARK OFFICE
CERTIFICATE OF CORRECTION

PATENT NO. : 11,214,597 B2
APPLICATION NO. : 16/227075
DATED : January 4, 2022
INVENTOR(S) : Harel et al.

It is certified that error appears in the above-identified patent and that said Letters Patent is hereby corrected as shown below:

On the Title Page

Item (57) in the ABSTRACT:
Line 3, "formation" should read --formulation--.
Line 5, "formulation agent" should read --formulation--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*